(12) United States Patent
Mizota et al.

(10) Patent No.: US 8,210,043 B2
(45) Date of Patent: Jul. 3, 2012

(54) ULTRASONIC MEASUREMENT METHOD, ULTRASONIC MEASUREMENT APPARATUS, AND ULTRASONIC SENSOR

(75) Inventors: Hirohisa Mizota, Hitachi (JP); Naoyuki Kono, Mito (JP); Atsushi Baba, Tokai (JP)

(73) Assignee: Hitachi-GE Nuclear Energy, Ltd., Hitachi-shi (JP)

( * ) Notice: Subject to any disclaimer, the term of this patent is extended or adjusted under 35 U.S.C. 154(b) by 313 days.

(21) Appl. No.: 12/754,264

(22) Filed: Apr. 5, 2010

(65) Prior Publication Data

US 2010/0251821 A1 Oct. 7, 2010

(30) Foreign Application Priority Data

Apr. 6, 2009 (JP) ................................ 2009-091864
Sep. 28, 2009 (JP) ................................ 2009-222818

(51) Int. Cl.
 *G01N 29/04* (2006.01)
(52) U.S. Cl. ............................................ 73/602; 73/628
(58) Field of Classification Search .................... 73/602, 73/628, 618, 626, 632, 633; 600/443, 447
See application file for complete search history.

(56) References Cited

U.S. PATENT DOCUMENTS

| | | | | |
|---|---|---|---|---|
| 5,677,491 A | * | 10/1997 | Ishrak et al. | 73/641 |
| 5,744,898 A | * | 4/1998 | Smith et al. | 310/334 |
| 5,902,242 A | * | 5/1999 | Ustuner et al. | 600/443 |
| 6,368,281 B1 | * | 4/2002 | Solomon et al. | 600/459 |
| 6,483,228 B2 | * | 11/2002 | Hashimoto | 310/336 |
| 7,263,888 B2 | * | 9/2007 | Barshinger et al. | 73/606 |
| 7,280,435 B2 | * | 10/2007 | Thomenius et al. | 367/153 |
| 7,658,110 B2 | * | 2/2010 | Fukukita | 73/620 |
| 7,708,691 B2 | * | 5/2010 | Lin | 600/437 |

FOREIGN PATENT DOCUMENTS

| | | |
|---|---|---|
| JP | 5-244691 A | 9/1993 |
| JP | 2003-599 A | 1/2003 |
| JP | 2005-351718 A | 12/2005 |

* cited by examiner

*Primary Examiner* — J M Saint Surin
(74) *Attorney, Agent, or Firm* — Crowell & Moring LLP

(57) ABSTRACT

An ultrasonic measurement method and an ultrasonic measurement apparatus are capable of performing an inspection for a short time with a high SN ratio and a small variation (that depends on an inspection direction) in sensitivity in a process for detecting a defect in all directions at 360 degrees using a matrix array sensor without performing mechanical scanning in all directions, while reducing noise that is caused by a bottom surface echo. An element selecting circuit selects a group of a plurality of ultrasonic transducer elements for transmission from among ultrasonic transducer elements that constitute a two-dimensional array sensor so that the ultrasonic transducer elements for selected for transmission are arranged in line symmetry with respect to a first line symmetric axis to set the group selected for transmission.

10 Claims, 28 Drawing Sheets

FIG.4

| PATTERN OF ELEMENTS TO BE USED / ELEMENT NUMBER / PATTERN | 1 | | 2 | | 3 | | ... | | N | |
|---|---|---|---|---|---|---|---|---|---|---|
| | P | R | P | R | P | R | P | R | P | R |
| A | 1 | 0 | 1 | 0 | 1 | 0 | ... | ... | 1 | 0 |
| B | 0 | 1 | 1 | 0 | 1 | 0 | ... | ... | 1 | 0 |
| C | 0 | 1 | 0 | 1 | 1 | 0 | ... | ... | 1 | 0 |
| D | 0 | 1 | 0 | 1 | 0 | 1 | ... | ... | 1 | 0 |
| E | 0 | 1 | 0 | 1 | 0 | 1 | ... | ... | 1 | 1 |
| ⋮ | ⋮ | ⋮ | ⋮ | ⋮ | ⋮ | ⋮ | ⋮ | ⋮ | ⋮ | ⋮ |

FIG.6

| DELAY TIME ELEMENT NUMBER / FOCAL POINT F (i) | 1 | | 2 | | ... | N | | PATTERN OF SELECTION OF ELEMENTS TO BE USED |
|---|---|---|---|---|---|---|---|---|
| | P | R | P | R | ... | P | R | |
| i = 1 | T11 | R11 | T12 | R12 | ... | T1n | R1n | A |
| i = 2 | T21 | R21 | T21 | R22 | ... | T2n | R2n | A |
| i = 3 | ... | ... | ... | ... | ... | ... | ... | B |
| i = 4 | ... | ... | ... | ... | ... | ... | ... | B |
| i = 5 | ... | ... | ... | ... | ... | ... | ... | C |
| ⋮ | ⋮ | ⋮ | ⋮ | ⋮ | ⋮ | ⋮ | ⋮ | ⋮ |

FIG.7

| DELAY TIME ELEMENT NUMBER FOCAL POINT F (i) | 1 | | 2 | | ... | N | |
|---|---|---|---|---|---|---|---|
| | P | R | P | R | ... | P | R |
| i = 1 | T11 | −1 | −1 | R12 | ... | T1N | −1 |
| i = 2 | −1 | R21 | T22 | −1 | ... | −1 | T2n |
| i = 3 | ... | ... | ... | ... | ... | ... | ... |
| i = 4 | ... | ... | ... | ... | ... | ... | ... |
| i = 5 | ... | ... | ... | ... | ... | ... | ... |
| ⋮ | ⋮ | ⋮ | ⋮ | ⋮ | ⋮ | ⋮ | ⋮ |

FIG.8
(A)
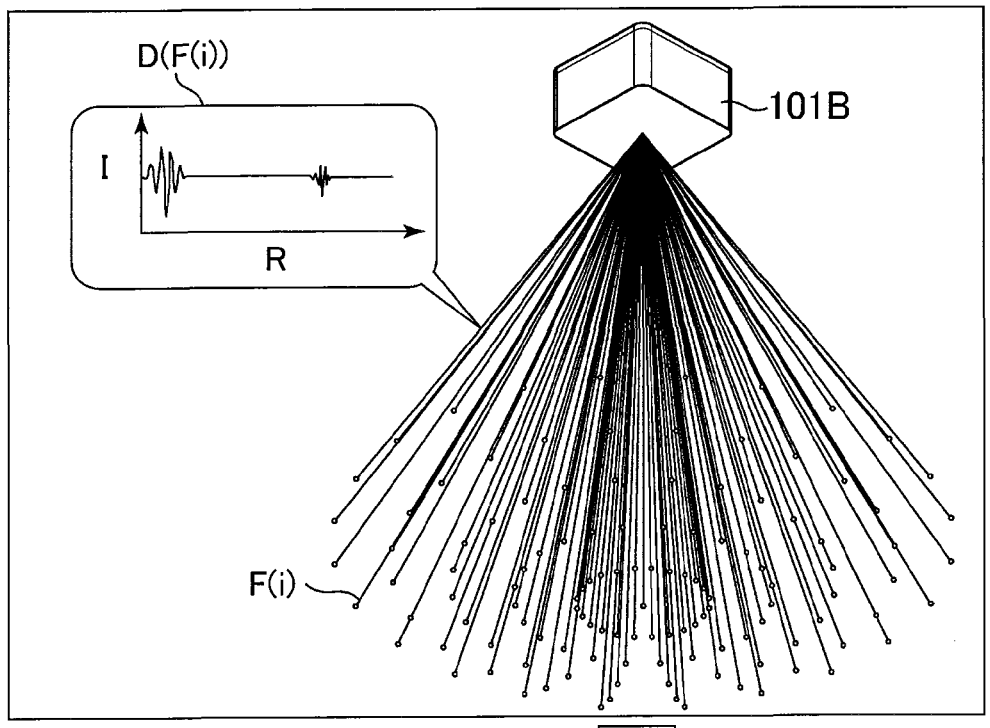
(B)
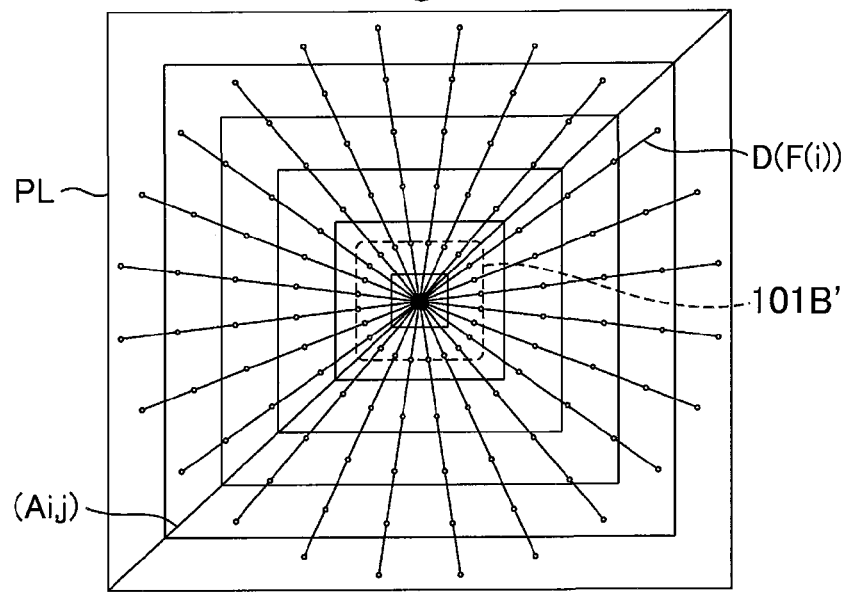

FIG.31

| PATTERN OF ELEMENTS TO BE USED / ELEMENT NUMBER / PATTERN | 1 | 2 | 3 | ... | | N |
|---|---|---|---|---|---|---|
| A | 0 | 0 | 0 | ... | ... | 1 |
| B | 0 | 0 | 1 | ... | ... | 1 |
| C | 0 | 1 | 1 | ... | ... | 1 |
| D | 1 | 1 | 1 | ... | ... | 0 |
| E | 1 | 1 | 0 | ... | ... | 0 |
| ⋮ | ⋮ | ⋮ | ⋮ | ⋮ | ⋮ | ⋮ |

ULTRASONIC MEASUREMENT METHOD, ULTRASONIC MEASUREMENT APPARATUS, AND ULTRASONIC SENSOR

BACKGROUND OF THE INVENTION

1. Field of the Invention

The present invention relates to an ultrasonic measurement method and an ultrasonic measurement apparatus. The invention more particularly relates to an ultrasonic measurement method and an ultrasonic measurement apparatus, which are suitable to use phased array transducer (array sensor) having ultrasonic transducer elements that are two-dimensionally arranged, and to the ultrasonic sensor.

2. Description of the Related Art

In a conventional technique, when it is difficult to predict a direction in which a defect will become larger, the defect may be overlooked in an ultrasonic inspection process for transmitting an ultrasonic wave in an axial direction and a circumferential direction. Thus, there is demand for an ultrasonic inspection process for transmitting an ultrasonic wave in all directions. Since this type of defect is detected by an angle beam inspection process, an ultrasonic inspection technique that simultaneously achieves those inspection processes is essential. In addition, in order to respond to demand for a reduction in an inspection time, it is necessary to develop a technique that is capable of performing an ultrasonic inspection process for transmitting an ultrasonic wave in all directions without mechanical scanning.

On the other hand, when a fixed-angle sensor is used, mechanical rotary scanning needs to be performed. In this case, in order to change an incident angle of an ultrasonic wave, the sensor needs to be replaced. Thus, it takes a long time for a measurement. A linear array sensor having ultrasonic transducer elements that are one-dimensionally arranged is capable of performing two-dimension-like scanning by means of a phased array technique in which the timing for applying an electric signal to each ultrasonic transducer element is controlled so that an ultrasonic beam converges at any refraction angle in a direction in which the elements are arranged. Thus, it is not necessary to replace the sensor. However, in order to perform a measurement in all directions, mechanical rotary scanning needs to be performed for the same reason as in the measurement using the fixed-angle sensor. Therefore, it takes a long time for the measurement.

In recent years, a phased array technique that uses a matrix array sensor having ultrasonic transducer elements two-dimensionally arranged has been actively researched and developed in order to reduce the measurement time (for example, refer to JP-A-2005-351718). In this method, it is possible to three-dimensionally transmit and receive an ultrasonic wave by controlling the timing for applying an electric signal in a manner similar to that in the linear array sensor; therefore, it is possible to perform a measurement in all directions for a short time without performing mechanical rotary scanning while obtaining a good signal-to-noise (SN) ratio.

The present inventors have studied on a three-dimensional ultrasonic technique that uses a matrix array sensor to inspect a plate material having a large thickness.

It is necessary that a sensor aperture through which an ultrasonic wave is transmitted and received be larger in order to determine whether or not a crack exists in a deep portion of the plate material in an inspect method using the three-dimensional ultrasonic technique.

When the size of a sensor aperture of a matrix array sensor constituted by ultrasonic transducer elements whose areas are approximately the same is increased in a manner similar to that in a conventional rectangular matrix sensor or a segmented sensor array, the number of ultrasonic transducer elements is increased in proportion to the square of the size of the sensor aperture.

However, the number of the ultrasonic transducer elements that can be controlled by a phased array apparatus is restricted for a technical reason. In addition, even when the number of the ultrasonic transducer elements that can be controlled by the phased array apparatus is increased, the apparatus would be larger and more expensive; therefore it is difficult to increase the size of a sensor aperture. In addition, performing a measurement in all directions at 360 degrees using a conventional rectangular matrix array sensor may cause a variation in sensitivity due to symmetry of the arrangement of ultrasonic transducer elements constituting the array sensor or due to the shapes of the ultrasonic transducer elements.

To avoid the above problems, a method is known which selects, from among ultrasonic transducer elements that are two-dimensionally arranged and constitute an array sensor, only a group of ultrasonic transducer elements that are arranged in a direction in which electronic scanning is performed and uses the selected elements to transmit and receive an ultrasonic wave (for example, refer to JP-5-244691-A).

In addition, another method is known which selects a transmitting element and a receiving element in a zigzag manner from among ultrasonic transducer elements that constitute an array sensor and are two-dimensionally arranged and uses the selected elements to transmit and receive an ultrasonic wave (for example, refer to JP-2003-599-A).

SUMMARY OF THE INVENTION

In the method described in JP-5-244691-A, however, since an ultrasonic wave spreads in a direction perpendicular to a scanning direction in a similar manner to an ultrasonic wave transmitted by a linear array sensor, an effect (that is specific to a matrix array sensor and is hereinafter referred to as a point focusing effect) in which the ultrasonic wave is three-dimensionally focused on a point cannot disadvantageously be obtained.

In addition, when an angle at which a defect exists in a measurement angle range (that is close to a normal direction) in which an ultrasonic wave propagates, the ultrasonic wave is reflected from a back surface of an object to be measured and detected as an echo (bottom surface echo) generated from a bottom surface. In this range, the echo becomes noise for a corner echo that is caused by a defect that exists on or near the back surface of the object. Even in a range other than the aforementioned range, a high-frequency grating lobe is reflected from the bottom surface and becomes noise in a similar manner.

The technique described in JP-2003-599-A alternately selects transmitting elements and receiving elements from among ultrasonic transducer elements that constitute an array sensor and are two-dimensionally arranged in 8 rows and 8 columns so that the selected transmitting elements are arranged in every other row and every other column and the selected receiving elements are arranged in every other row and every other column, as shown in FIG. 1 of JP-2003-599-A. Thus, a distance between each adjacent pair of the selected transmitting elements and a distance between each adjacent pair of the selected receiving elements are twice as large as those in the case in which all the ultrasonic transducer elements are used as transmitting elements or receiving elements. When the distance between each adjacent pair of the transmitting elements and the distance between each adjacent pair of the receiving elements are large, a grating lobe is generated in a range in which a defect is detected. Thus, the defect is superimposed on the grating lobe. As a result, the defect may not be detected.

An object of the present invention is to provide an ultrasonic measurement method and an ultrasonic measurement apparatus, which are capable of performing a measurement for a short time with a high SN ratio and a small variation (that depends on an inspection direction) in sensitivity by transmitting and receiving an ultrasonic wave to and from a region (that is to be measured) in a process for detecting a defect in all directions at 360 degrees using a matrix array sensor without performing mechanical scanning in all directions, while maintaining an effect in which the ultrasonic wave is focused on a point and reducing noise that is caused by a bottom surface echo.

According to the technique described in JP-5-244691-A, when an array sensor (having ultrasonic transducer elements arranged in angular ranges that are the same) or an array sensor (having ultrasonic transducer elements that are not formed in a disk-like shape and having a single ultrasonic transducer element that is arranged at the innermost circumference of the sensor and is formed in a disk shape) is used, the sizes of ultrasonic transducer elements arranged on an inner circumferential side of the sensor are small depending on the angular range. Thus, it is difficult to process the sensor during a wiring process on the sensor. In addition, sufficient sensitivity cannot be obtained on the inner circumferential side of the sensor, and noise such as a side lobe may be increased.

According to the measurement method described in JP-A-5-244691 using the sensor that has the shape described in JP-A-5-244691, since the ultrasonic transducer elements arranged on the inner circumferential side are small, directionality of a sound is low and an SN ratio of an image obtained by an inspection cannot be improved.

Another object of the present invention is to provide an ultrasonic measurement apparatus that is suitable for inspecting a deep portion of a plate material having a large thickness with an improved SN ratio and is capable of having a large sensor aperture, and to provide an ultrasonic measurement method and an ultrasonic sensor that is used in the ultrasonic measurement apparatus.

(1) In order to accomplish the aforementioned object, according to the present invention, an ultrasonic measurement method using a two-dimensional array sensor that has a plurality of ultrasonic transducer elements two-dimensionally arranged and using a wave reflected from an inner portion of an object that is to be measured, includes the steps of:

selecting a group of a plurality of ultrasonic transducer elements for transmission from among the ultrasonic transducer elements that constitute the two-dimensional array sensor so that the ultrasonic transducer elements selected for transmission are arranged in line symmetry with respect to a first line symmetric axis and setting the group selected for transmission, and selecting a group of a plurality of ultrasonic transducer elements for reception from among the ultrasonic transducer elements that constitute the two-dimensional array sensor so that the ultrasonic transducer elements selected for reception are arranged in line symmetry with respect to a second line symmetric axis that is perpendicular to the first line symmetric axis and passes through a rotationally symmetric axis and setting the group selected for reception;

transmitting an ultrasonic wave in the direction of the first line symmetric axis;

receiving an ultrasonic wave from the direction of the second line symmetric axis to store a signal reflected from the inner portion of the object; and processing the reflected signal to inspect the object.

In the method, it is possible to perform an inspection for a short time with a high SN ratio and a small variation (that depends on an inspection direction) in sensitivity by transmitting and receiving an ultrasonic wave to and from a region (that is to be measured) in a process for detecting a defect in all directions at 360 degrees using a matrix array sensor without performing mechanical scanning in all directions, while maintaining an effect in which the ultrasonic wave is focused on a point and reducing noise that is caused by a bottom surface echo.

(2) Preferably, the ultrasonic measurement method described in the item (1) further may include the steps of:

selecting a group of a plurality of ultrasonic transducer elements for transmission from among the ultrasonic transducer elements that constitute the two-dimensional array sensor so that the ultrasonic transducer elements selected for transmission are arranged in line symmetry with respect to a third line symmetric axis that is set by rotating the first line symmetric axis by a predetermined angle with respect to the rotationally symmetric axis, and selecting a group of a plurality of ultrasonic transducer elements for reception from among the ultrasonic transducer elements that constitute the two-dimensional array sensor so that the ultrasonic transducer elements selected for reception are arranged in line symmetry with respect to a fourth line symmetric axis that is perpendicular to the third line symmetric axis and passes through the rotationally symmetric axis;

transmitting an ultrasonic wave in the direction of the third line symmetric axis;

receiving an ultrasonic wave from the direction of the fourth line symmetric axis to store a signal reflected from the inner portion of the object; and processing the reflected signal to inspect the object.

(3) In the ultrasonic measurement method described in the item (1), the group of the ultrasonic transducer elements selected for transmission and the group of the ultrasonic transducer elements selected for reception may preferably be arranged so that when the groups are rotated about the rotationally symmetric axis by 90 degrees, the groups overlap each other.

(4) Preferably, the ultrasonic measurement method described in the item (1) further may include the steps of:

setting a plurality of focal points to which ultrasonic waves are to be transmitted by the two-dimensional array sensor;

storing signals reflected from the focal points that are located in the inner portion of the object; and processing the stored reflected signals to two-dimensionally or three-dimensionally image the inner portion of the object and display an image of the inner portion of the object.

(5) Preferably, the ultrasonic measurement method described in the item (4) further may include the step of projecting three-dimensionally stored inspection data onto a flat plane and two-dimensionally displaying the data on an inspection result display screen.

(6) Preferably, the ultrasonic measurement method described in the item (5) further may include the step of displaying information on a refraction angle $\phi$, an azimuth angle $\theta$ and a reflected intensity I.

(7) Preferably, the ultrasonic measurement method described in the item (6) further may include the step of specifying a range of the refraction angle $\phi$ to be displayed.

(8) Preferably, the ultrasonic measurement method described in the item (7) further may include the steps of:

performing either an operation for weighting a pulse voltage that is to be applied to each ultrasonic transducer element selected for transmission before the transmission of the ultrasonic wave or an operation for weighting a signal received when the ultrasonic wave is received; and calibrating reflection data and a reflected intensity.

(9) In order to accomplish the aforementioned object, according to the present invention, an ultrasonic measurement apparatus includes:

a two-dimensional array sensor having a plurality of ultrasonic transducer elements two-dimensionally arranged;

a transmitting/receiving section that transmits an ultrasonic wave from each ultrasonic transducer element included in the two-dimensional array sensor to an object to be measured and receives a wave reflected from the object;

a controller that controls the transmitting/receiving section to generate three-dimensional or two-dimensional image data; and a display unit that displays the three-dimensional or two-dimensional image data generated by the controller, wherein the controller includes an element selecting section that selects a group of a plurality of ultrasonic transducer elements for transmission from among the ultrasonic transducer elements that constitute the two-dimensional array sensor so that the ultrasonic transducer elements selected for transmission are arranged in line symmetry with respect to a first line symmetric axis to set the group selected for transmission, and selects a group of a plurality of ultrasonic transducer elements for reception from among the ultrasonic transducer elements that constitute the two-dimensional array sensor so that the ultrasonic transducer elements selected for reception are arranged in line symmetry with respect to a second line symmetric axis that is perpendicular to the first line symmetric axis and passes through a rotationally symmetric axis to set the group selected for reception, and the transmitting/receiving section includes a transmitting element selector and a receiving element selector, the transmitting element selector being adapted to select, as transmitting elements, the ultrasonic transducer elements set by the element selecting section, the receiving element selector being adapted to select, as receiving elements, the ultrasonic transducer elements set by the element selecting section.

The ultrasonic measurement apparatus is capable of performing an inspection for a short time with a high SN ratio and a small variation (that depends on an inspection direction) in sensitivity by transmitting and receiving an ultrasonic wave to and from a region (that is to be measured) in a process for detecting a defect in all directions at 360 degrees using a matrix array sensor without performing mechanical scanning in all directions, while maintaining an effect in which the ultrasonic wave is focused on a point and reducing noise that is caused by a bottom surface echo.

(10) In the ultrasonic measurement apparatus described in the item (9), the controller preferably may include either an amplitude adjusting section or a weighting section, the amplitude adjusting section being adapted to weight a pulse voltage that is to be applied to each ultrasonic transducer element selected for transmission before the transmission of the ultrasonic wave, the weighting section being adapted to weight a signal received when the ultrasonic wave is received.

(2-1) In order to accomplish the aforementioned object, according to the present invention, an ultrasonic measurement apparatus includes:

a two-dimensional array sensor having a plurality of ultrasonic transducer elements two-dimensionally arranged;

a transmitting/receiving section that transmits an ultrasonic wave from the two-dimensional array sensor and receives a wave reflected from an inner portion of an object that is to be measured; and a controller that controls the transmitting/receiving section to cause the transmitting/receiving section to transmit the ultrasonic wave and receive the ultrasonic wave;

wherein the two-dimensional array sensor has an inner circumferential portion and an outer circumferential portion, the arrangement of the ultrasonic transducer elements included in the inner circumferential portion being different from the arrangement of the ultrasonic transducer elements included in the outer circumferential portion, a distance between the gravity centers of each adjacent pair of the ultrasonic transducer elements included in the inner circumferential portion is equal to or less than a distance at which noise such as a grating lobe is not caused, a distance between the gravity centers of each adjacent pair of some of the ultrasonic transducer elements included in the outer circumferential portion is equal to or less than the distance at which noise such as a grating lobe is not caused, and a distance between the gravity centers of each adjacent pair of the other ultrasonic transducer elements included in the outer circumferential portion is larger than the distance at which such as a grating lobe is not caused, the controller has an element selecting circuit that selects an element that is to be used from among the plurality of ultrasonic transducer elements that constitute the two-dimensional array sensor, the element selecting circuit selects all the ultrasonic transducer elements included in the inner circumferential portion and ultrasonic transducer elements included in the outer circumferential portion so that a distance between the gravity centers of each adjacent pair of the selected transducer elements included in the outer circumferential portion, wherein the distance is measured in a transmitting and receiving direction obtained by projecting a direction in which an ultrasonic is transmitted and received onto a surface of the array sensor, is equal to or less than the distance at which noise is not caused.

The ultrasonic measurement apparatus described in the item (11) is suitable for inspecting a deep portion of a plate material having a large thickness with an improved SN ratio and is capable of having a large sensor aperture.

(2-2) In the ultrasonic measurement apparatus described in the item (2-1), the element selecting circuit may preferably select elements whose gravity centers are located in a rectangular region having a long side that extends in the projected transmitting and receiving direction and a short side whose length is equal to the diameter of the inner circumferential portion.

(2-3) To accomplish the aforementioned object, according to the present invention, an ultrasonic sensor that transmits an ultrasonic wave and has a plurality of two-dimensionally ultrasonic transducer elements arranged, the ultrasonic sensor being used in an ultrasonic measurement apparatus that performs an inspection using a wave reflected from an inner portion of an object that is to be measured, includes:

an inner circumferential portion and an outer circumferential portion in which the arrangement of the ultrasonic transducer elements included in the inner circumferential portion is different from the arrangement of the ultrasonic transducer elements included in the outer circumferential portion, wherein a distance between the gravity centers of each adjacent pair of the ultrasonic transducer elements included in the inner circumferential portion is equal to or less than a distance at which such as a grating lobe is not caused, and a distance between the gravity centers of each adjacent pair of some of the ultrasonic transducer elements included in the outer circumferential portion is equal to or less than the distance at which noise such as a grating lobe is not caused, and a distance between the gravity centers of each adjacent pair of the other ultrasonic transducer elements included in the outer circumferential portion is larger than the distance at which noise such as a grating lobe is not caused.

The ultrasonic sensor is suitable for inspecting a deep portion of a plate material having a large thickness with an improved SN ratio and is capable of having a large sensor aperture.

(2-4) To accomplish the aforementioned object, according to the present invention, an ultrasonic measurement method using a two-dimensional array sensor that has a plurality of ultrasonic transducer elements two-dimensionally arranged to transmit an ultrasonic wave and using a wave reflected from an inner portion of an object that is to be measured, includes the steps of:

using the two-dimensional array sensor that has an inner circumferential portion and an outer circumferential portion, the arrangement of the ultrasonic transducer elements included in the inner circumferential portion being different from the arrangement of the ultrasonic transducer elements included in the outer circumferential portion, wherein a distance between the gravity centers of each adjacent pair of the ultrasonic transducer elements included in the inner circumferential portion is equal to or less than a distance at which noise such as a grating lobe is not caused, a distance between the gravity centers of each adjacent pair of some of the ultrasonic transducer elements included in the outer circumferential portion is equal to or less than the distance at which noise is caused, and a distance between the gravity centers of each adjacent pair of the other the ultrasonic transducer elements included in the outer circumferential portion is larger than the distance at which noise is not caused; and selecting all the ultrasonic transducer elements included in the inner circumferential portion and ultrasonic transducer elements that are adjacent to each other and included in the outer circumferential portion and whose gravity centers are separated with a distance that is equal to or less than the distance at which noise is not caused for the inspection of the object, the distance between the gravity centers of each adjacent pair of the selected elements included in the outer circumferential portion being measured in a direction obtained by projecting, onto the surface of the array sensor, a direction in which the ultrasonic wave is transmitted and received.

The ultrasonic measurement method described in the item (2-4) is suitable for inspecting a deep portion of a plate material having a large thickness with an improved SN ratio and is capable of having a large sensor aperture.

(2-5) Preferably, the ultrasonic measurement method described in the item (2-4) further may include the steps of:

setting a plurality of focal points to which ultrasonic waves are to be transmitted by the two-dimensional array sensor;

selecting a range of elements to be used for transmission and reception of the ultrasonic waves to the focal points;

storing signals reflected from the focal points located in the inner portion of the object; and processing the stored reflected signals to two-dimensionally or three-dimensionally image the inner portion of the object.

According to the invention, it is possible to perform an inspection for a short time with a high SN ratio and a small variation (that depends on an inspection direction) in sensitivity by transmitting and receiving an ultrasonic wave to and from a region (that is to be measured) in a process for detecting a defect in all directions at 360 degrees using a matrix array sensor without performing mechanical scanning in all directions, while maintaining an effect in which the ultrasonic wave is focused on a point and reducing noise that is caused by a bottom surface echo.

According to another invention, the ultrasonic measurement apparatus is suitable for inspecting a deep portion of a plate material having a large thickness with an improved SN ratio and is capable of having a large sensor aperture.

BRIEF DESCRIPTION OF THE DRAWINGS

FIG. 4 is a diagram showing a table that indicates combinations of ultrasonic transducer elements that are to be used for transmission and reception and are included in the ultrasonic measurement apparatus according to the first embodiment of the present invention.

FIG. 6 is a diagram showing another table that indicates combinations of ultrasonic transducer elements that are to be used for transmission and reception and are included in the ultrasonic measurement apparatus according to the first embodiment of the present invention.

FIG. 7 is a diagram showing another table that indicates combinations of ultrasonic transducer elements that are to be used for transmission and reception and are included in the ultrasonic measurement apparatus according to the first embodiment of the present invention.

FIGS. 8A and 8B are diagrams each showing an imaging operation that is performed by the ultrasonic measurement apparatus according to the first embodiment of the present invention.

FIG. 31 is a diagram showing a pattern of elements that are to be used and are included in the ultrasonic measurement apparatus according to the fifth embodiment of the present invention.

DESCRIPTION OF THE PREFERRED EMBODIMENTS

The configuration and operations of an ultrasonic measurement apparatus according to a first embodiment of the present invention are described with reference to FIGS. 1 to 17.

First, the entire configuration of the ultrasonic measurement apparatus according to the present embodiment is described with reference to FIG. 1.

Figure 1:
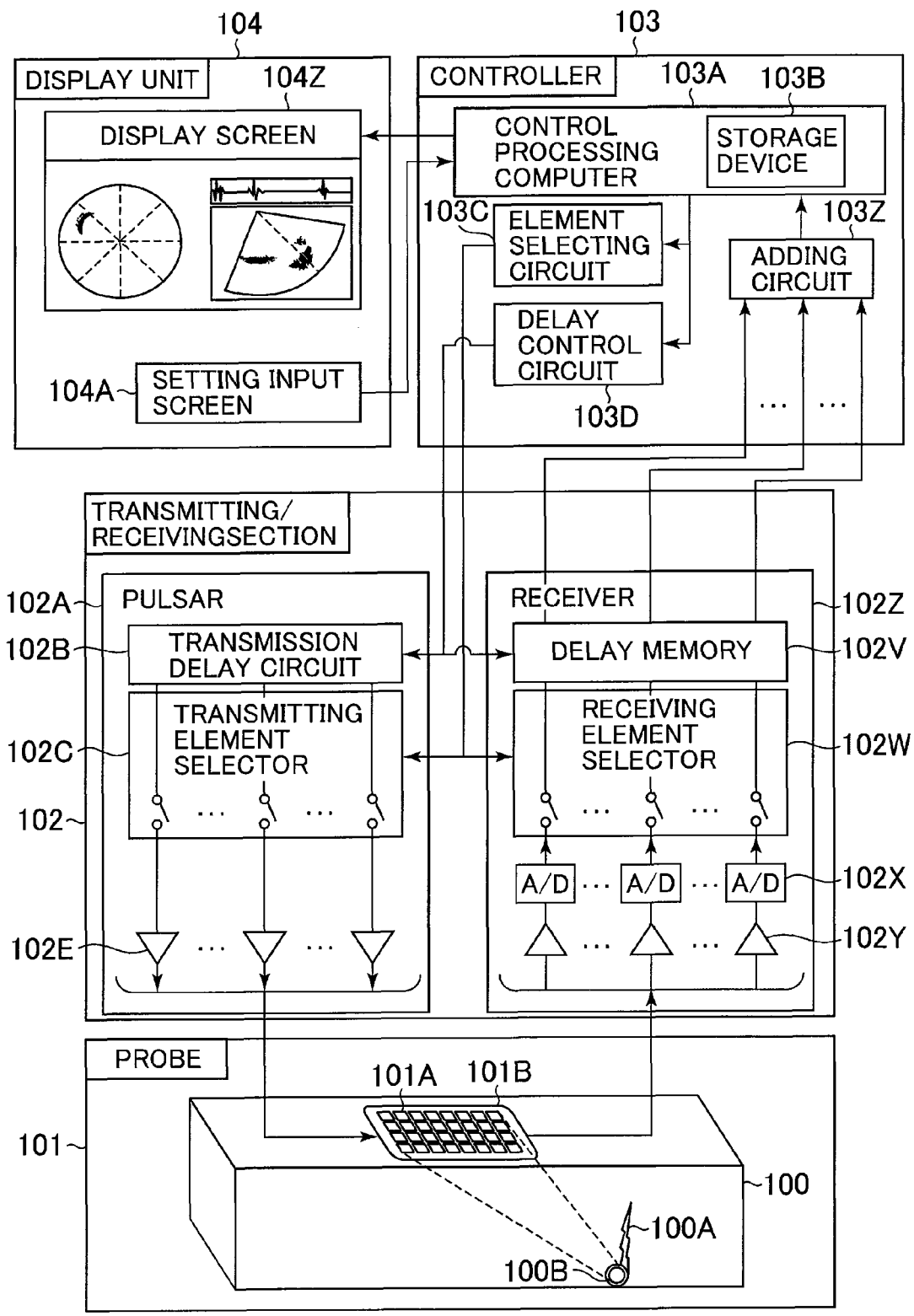
FIG. 1 is a block diagram showing the entire configuration of an ultrasonic measurement apparatus according to a first embodiment of the present invention.

FIG. 1 is a block diagram showing the entire configuration of the ultrasonic measurement apparatus according to the present embodiment.

The ultrasonic measurement apparatus according to the present embodiment measures an object 100 and a reflection source 100A located inside the object or located on the surface of the object with an excellent SN ratio. The ultrasonic measurement apparatus according to the present embodiment has a probe 101, a transmitting/receiving section 102, a controller 103, and a display unit 104.

The probe 101 includes an array sensor 101B that transmits and receives an ultrasonic wave to the object 100 that is to be measured. The array sensor 101B has a plurality of ultrasonic transducer elements 101A.

The transmitting/receiving section 102 has a pulsar 102A and a receiver 102Z. The pulsar 102A provides a delay time to the array sensor 101B so that the array sensor 101B transmits an ultrasonic wave on the basis of the delay time. The receiver 102Z receives an ultrasonic wave, and converts the received analog ultrasonic wave into a digital signal as a reception signal.

The controller 103 has a control processing computer 103A, an element selecting circuit 103C, a delay time control circuit 103D, and an adding circuit 103Z. The control processing computer 103A has a storage device 103B. The element selecting circuit 103C controls the ultrasonic transducer elements 101A when necessary. Specifically, the element selecting circuit 103C switches between ultrasonic transducer elements 101A that are to be used for transmission of an ultrasonic wave and switches between ultrasonic transducer elements 101A that are to be used for reception of an ultrasonic wave. The delay time control circuit 103D controls the delay time that is used for transmission of an ultrasonic wave and a delay time that is used for reception of an ultrasonic wave. The adding circuit 103Z receives a plurality of signals from the receiver 102Z and adds the received signals. The control processing computer 103A controls the element selecting circuit 103O, the delay time control circuit 103D and the adding circuit 103Z and stores a received signal in the storage device 103B. The control processing computer 103A performs processing on the received signal.

The display unit 104 has a setting input screen 104A and a display screen 104Z. Various settings can be displayed on the setting input screen 104A and can be input using the setting input screen 104A. A signal received by the display unit 104 and an image obtained by a measurement are displayed on the display screen 104Z.

Next, operations of the sections of the apparatus are described below.

The control processing computer 103A transmits a transmitting/receiving element switching signal that is used to select an ultrasonic transducer element to be used to transmit/receive an ultrasonic wave to the element selecting circuit 103C upon storing a reflection signal received from the object that is to be measured by transmission and reception of the ultrasonic wave. In addition, the control processing computer 103A provides, through the delay control circuit 103D, a delay time to each ultrasonic transducer element so that the element transmits an ultrasonic wave that will be focused and receives an ultrasonic wave.

A transmission delay circuit 102B receives the transmitted signal and the delay time and transmits the signal (transmission signal) to a transmitting element selector 102C after a time specified by the received delay time.

The transmitting element selector 102C receives the transmission signal having the delay time added thereto from the transmission delay circuit 102B. The transmitting element selector 102C then selects a transmitting element on the basis of a selection signal (that is used to select the transmitting element) transmitted from the element selecting circuit 103C and transmits the transmission signal to a transmission amplifier 102E. The transmitting element selector 102C selects a receiving element on the basis of a receiving element switching signal transmitted from the control processing computer 103A. The present embodiment is characterized in a method for selecting a transmitting element and a receiving element by means of the transmitting element selector 102C, and the method is described in detail with reference to FIGS. 13 to 17.

The transmission amplifier 102E amplifies the transmission signal and applies, to the ultrasonic transducer elements 101A included in the array sensor 101B, a drive voltage that is used to transmit an ultrasonic wave. In this case, the transmitting element selector 102C is capable of separately transmitting signals to an N number of ultrasonic transducer elements 101A included in the array sensor 101B or simultaneously transmitting signals to a plurality of ultrasonic transducer elements 101A included in the array sensor 101B.

The plurality of ultrasonic transducer elements 101A receives the amplified signals and transmits ultrasonic waves by means of a piezoelectric effect. The present embodiment describes transmission and reception of ultrasonic waves by the ultrasonic transducer elements 101A included in the array sensor 101B.

As described above, when the delay time is added to the transmission signal and a voltage is applied to each ultrasonic transducer element 101A on the basis of the delay time, the ultrasonic transducer element 101A transmits an ultrasonic wave after the time specified by the delay time. In order to focus the ultrasonic waves on a certain point, a voltage is applied to each ultrasonic transducer element after a time specified by the delay time corresponding to a geometric distance between the ultrasonic transducer element and the focal point, i.e., the distance determined in consideration of the velocity of the ultrasonic wave in each medium and refraction at the boundary between the media. In this way, the ultrasonic waves are transmitted and focused (for example, when a defect 100A exists in the object 100 that is to be measured, the ultrasonic waves are focused on a focal point 100B so that the defect can be detected with a high SN ratio) on a predetermined portion of the object 100.

The receiver 102Z receives ultrasonic waves and processes electric signals generated by means of a piezoelectric effect. In order to process the electric signals, an amplifier 102Y receives signals (reception signals) corresponding to the ultrasonic waves received by the ultrasonic transducer elements 101A and amplifies the reception signals, and an analog-digital converter 102X converts the analog received signals into digital signals.

A receiving element selector 102W receives a signal from the receiving element selected by means of a command transmitted from the transmitting element selector 102C. The reception signal is converted into a digital signal, and selected and stored in a delay memory 102V. When the ultrasonic waves are focused on the focal point 100B in a similar manner to ultrasonic wave transmission and reception, the delay time transmitted from the delay control circuit 103D is added to the reception signal transmitted from each ultrasonic transducer element, and the signal having the delay time added thereto is stored in the delay memory 102V.

The adding circuit 103Z included in the controller 103 adds the reception signals and transmits the thus-obtained signal to the control processing computer 103A.

Next, a method for selecting a transmitting element and a receiving element, which are included in the ultrasonic measurement apparatus according to the present embodiment, is described below with reference to FIGS. 2 to 4.

Figure 2:
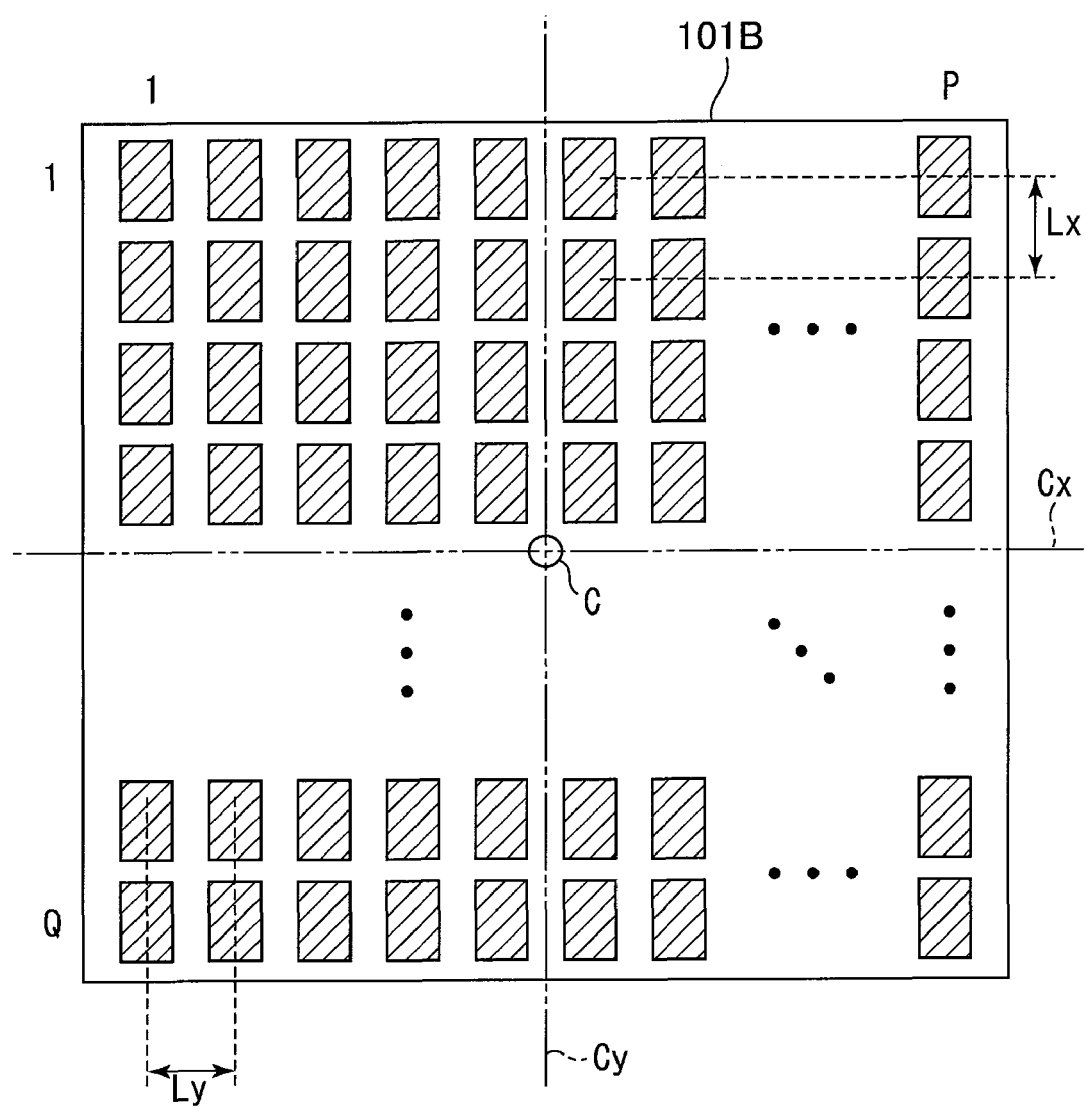
FIG. 2 is a diagram showing the configuration of a two-dimensional array sensor that is used in the ultrasonic measurement apparatus according to the first embodiment of the present invention.
Figure 3:
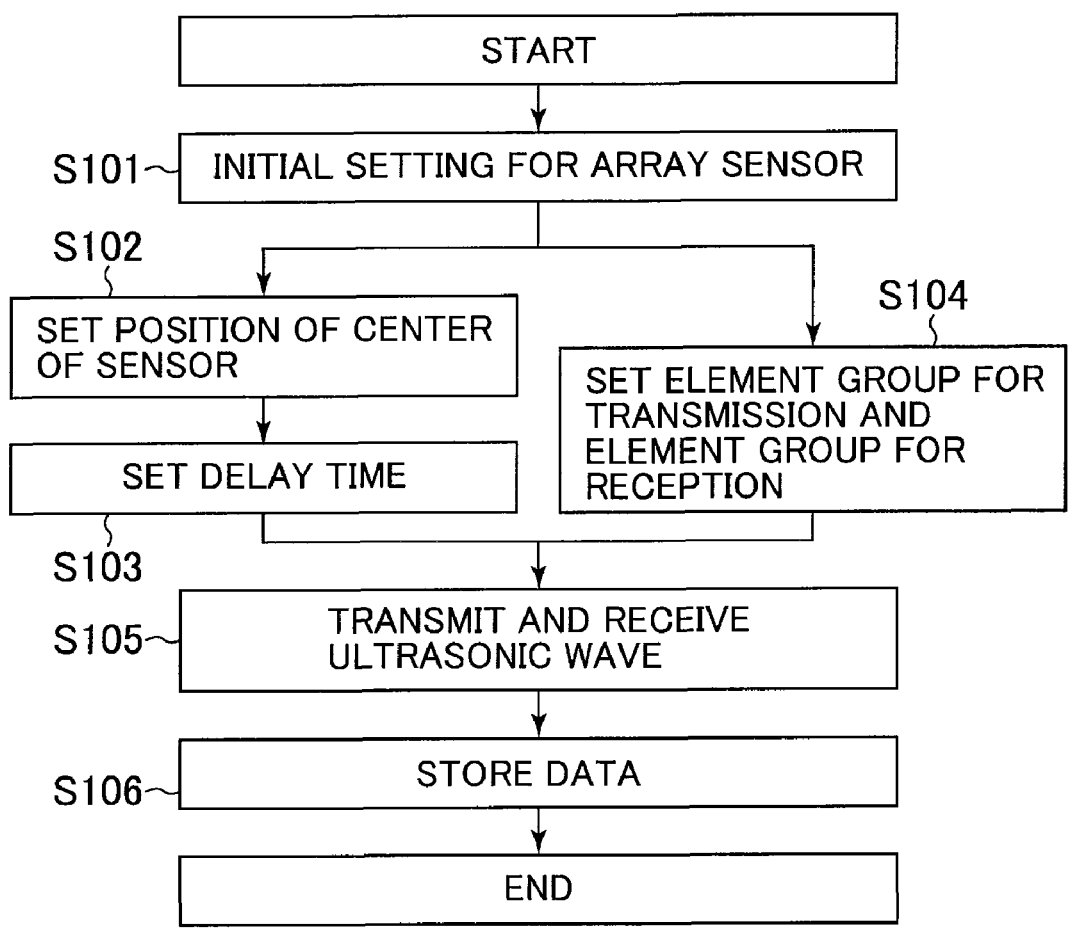
FIG. 3 is a flowchart of a method for selecting a transmitting element and a receiving element from among elements that are included in the ultrasonic measurement apparatus according to the first embodiment of the present invention.

FIG. 2 is a diagram showing the configuration of the two-dimensional array sensor that is used in the ultrasonic measurement apparatus according to the first embodiment of the present invention. FIG. 3 is a flowchart of a method for selecting a transmitting element and a receiving element, which are included in the ultrasonic measurement apparatus according to the first embodiment of the present invention. FIG. 4 is a diagram showing a table that indicates combinations of ultrasonic transducer elements that are to be used for transmission and reception and are included in the ultrasonic measurement apparatus according to the first embodiment of the present invention.

The following describes procedures for selecting an ultrasonic transducer element that is to be used to transmit/receive an ultrasonic wave so as to improve an SN ratio. The ultrasonic transducer elements are selected from among the elements included in the apparatus described with reference to FIG. 1.

In order to perform setting on the setting input screen 104A, the following information is necessary: the sizes, positions and arrangement of the ultrasonic transducer elements that constitute the array sensor.

FIG. 2 schematically shows the array sensor 101B having the ultrasonic transducer elements that are two-dimensionally arranged.

It is assumed that the array sensor 101B has an N number of ultrasonic transducer elements 101A arranged in P rows and Q columns (P×Q=N). In order to set the velocity of an ultrasonic wave to be transmitted to the object and to set the arrangement of the N number of ultrasonic transducer elements 101A that constitute the array sensor 101B and are two-dimensionally arranged and pitches between the ultrasonic transducer elements 101A, a pitch Lx between each adjacent pair of the ultrasonic transducer elements 101A arranged in a vertical direction and a pitch Ly between each adjacent pair of the ultrasonic transducer elements 101A arranged in a horizontal direction are set (shown in FIG. 2). Thus, the positions of the ultrasonic transducer elements 101A that are arranged in the array sensor 101B can be recognized.

Next, the procedures for the setting are described with reference to FIG. 3.

When the setting is started, an inspector uses the setting input screen 104A (shown in FIG. 1) to enter, as initial settings for the array sensor, necessary information such as information on the ultrasonic transducer elements that constitute the array sensor and the velocity of an ultrasonic wave in step S101.

Then, the position of the center of the sensor having the N number of ultrasonic transducer elements, which is a reference of the delay time and image display, is set in step S102. In general, the center (intersection of a central line Cy and a central line Cx) of the ultrasonic transducer elements is set as the center C of the sensor.

Next, the control processing computer 103A calculates a pattern of delay times for the respective ultrasonic transducer elements that are included in the array sensor in step S103.

Meanwhile, the element selecting circuit 103C uses the information provided in the initial setting of step S101 to set an ultrasonic transducer element group that is to be used for transmission and reception in step S104.

The transmitting/receiving section 102 transmits and receives an ultrasonic wave on the basis of these settings in step S105, and data is stored in step S106. Then, the process is ended.

In order to simply set a combination of ultrasonic transducer elements to be used for transmission and a combination of ultrasonic transducer elements to be used for reception, the following operations may be performed: data on combinations of ultrasonic transducer elements to be used for transmission and reception is pre-stored in the storage device 103B (shown in FIG. 1) included in the control processing computer 103A; a combination pattern of ultrasonic transducer elements to be used for transmission and reception is specified; the specified pattern is read when an inspection starts; the transmitting element selector 102C is operated in order to perform the transmission; and the receiving element selector 102W is operated in order to perform the reception.

FIG. 4 shows an example of the table that indicates combinations of ultrasonic transducer elements that are to be used for transmission and reception.

As shown in FIG. 4, combinations of ultrasonic transducer elements to be used for transmission and reception are arranged in a vertical direction of FIG. 4. Element numbers (for example, element numbers of the elements shown in FIG. 2) of the ultrasonic transducer elements constituting the array sensor are displayed. In addition, ON and OFF states of transmitting elements (P) 401 and receiving elements (R) 402 are displayed and indicated by 1 and 0, respectively. The transmitting elements (P) 401 and the receiving elements (R) 402 are the ultrasonic transducer elements.

Figure 5:
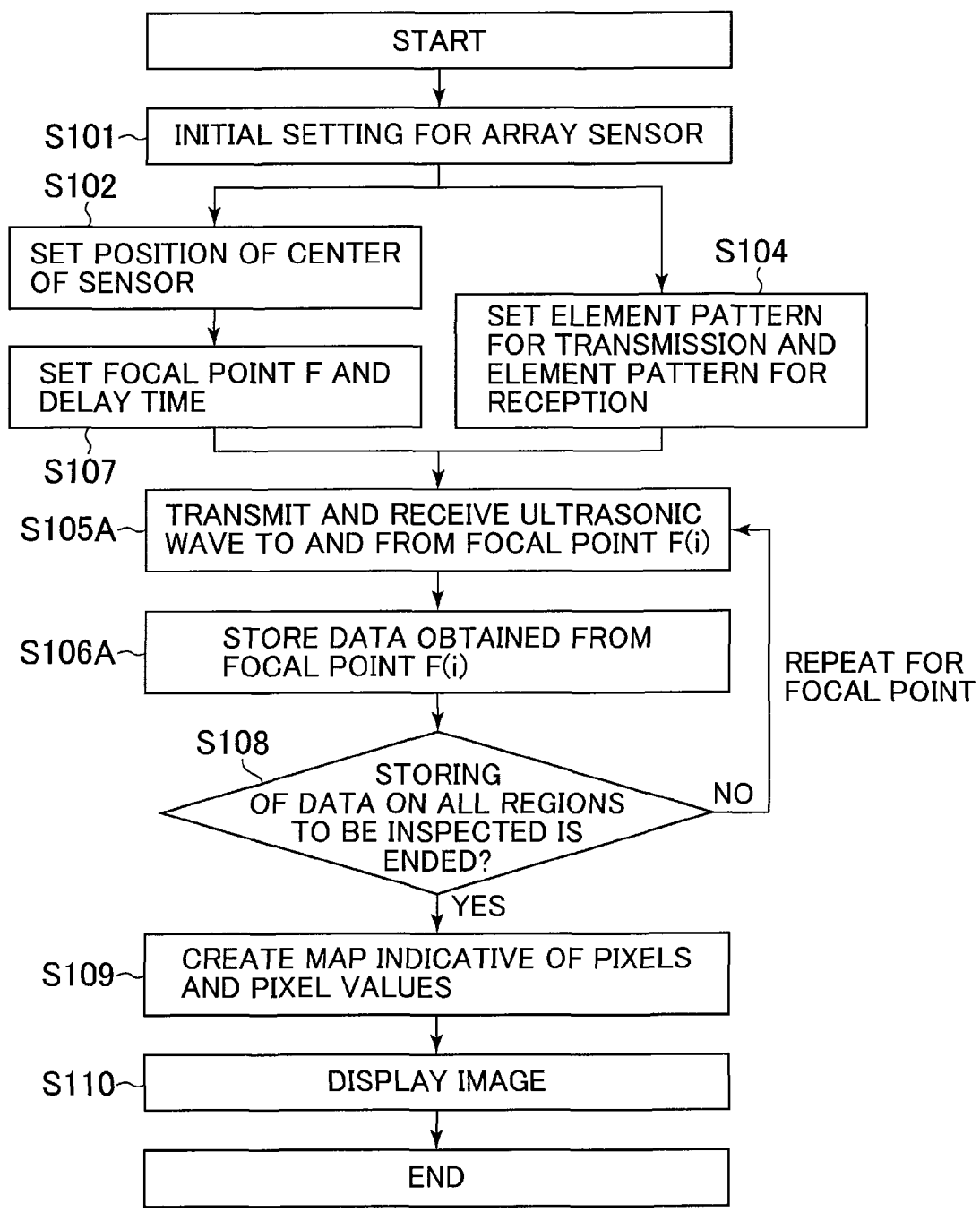
FIG. 5 is a flowchart of another method for selecting a transmitting element and a receiving element from among the elements that are included in the ultrasonic measurement apparatus according to the first embodiment of the present invention.

The following describes another method for selecting a transmitting element and a receiving element, which are included in the ultrasonic measurement apparatus according to the present embodiment with reference to FIGS. 5 to 7.

FIG. 5 is a flowchart of the method for selecting a transmitting element and a receiving element, which are included in the ultrasonic measurement apparatus according to the present embodiment. FIG. 6 is a diagram showing another table that indicates combinations of ultrasonic transducer elements that are to be used for transmission and reception and are included in the ultrasonic measurement apparatus according to the embodiment of the present invention. FIG. 7 is a diagram showing another table that indicates combinations of ultrasonic transducer elements that are to be used for transmission and reception and are included in the ultrasonic measurement apparatus according to the embodiment of the present invention.

FIG. 5 is a flowchart of the selection method that is performed on a plurality of focal points F (i).

When the setting is started, the inspector uses the setting input screen 104A (shown in FIG. 1) to enter, as initial settings for the array sensor, necessary information such as information on the ultrasonic transducer elements that constitute the array sensor and the velocity of an ultrasonic wave in step S101.

Then, the position of the center of the sensor having the N number of ultrasonic transducer elements, which is a reference of the delay time and image display, is set in step S102. In general, the center (intersection of the central line Cy and the central line Cx) of the ultrasonic transducer elements is set as the center C of the sensor.

Next, the control processing computer 103A calculates a focal point F (on which an ultrasonic wave transmitted by each ultrasonic transducer element included in the array sensor is focused) and a delay time (for transmission by each ultrasonic transducer element included in the array sensor) and sets the focal point F and the delay time in step S107.

Meanwhile, the element selecting circuit 103C uses the information provided in the initial setting of step S101 to set an ultrasonic transducer element group to be used for transmission and an ultrasonic transducer element group to be used for reception in step S104.

The transmitting/receiving section 102 transmits and receives ultrasonic waves as set in the aforementioned manner to and from each focal point F (i) in step S105A, and data (reflection data) obtained from the focal point F (i) is stored in step S106A.

It is determined whether or not data on all directions is completely stored in step S108. When the operation for storing the data on all the directions is not ended (or when the answer in step S108 is NO), the process returns to step S105A and an ultrasonic wave is transmitted to the next focal point F (i+1) and received from the focal point F (i+1). The operation for storing reflection data is sequentially repeated until reflection data on all regions to be measured is completely stored.

When the operation for storing the data on all the directions is ended (or when the answer in step S108 is YES), the control processing computer 103A creates a map indicative of pixels and pixel values in step S109 and causes an image to be displayed in step S110. Then, the process is ended.

In order to simply set a combination of ultrasonic transducer elements to be used for transmission and a combination of ultrasonic transducer elements to be used for reception, the following operations may be performed: the table (shown in FIG. 4) indicative of combinations of ultrasonic transducer elements to be used for transmission and combinations of ultrasonic transducer elements to be used for reception is pre-stored in the storage device 103B (shown in FIG. 1); a combination of ultrasonic transducer elements to be used for transmission and a combination of ultrasonic transducer elements to be used for reception are read when a measurement starts; the transmitting element selector 102C is operated in order to perform the transmission; and the receiving element selector 102W is operated in order to perform the reception.

FIG. 6 shows an example of a table that indicates a delay time that is to be given to each ultrasonic transducer element to be used for transmission and to each ultrasonic transducer element to be used for reception. Methods for setting a delay time are described in various documents. For example, a method for setting a delay time is described in a medical ultrasonic apparatus handbook.

A combination of ultrasonic transducer elements to be used to transmit ultrasonic waves to the focal points F (i) and a combination of ultrasonic transducer elements to be used to receive ultrasonic waves from the focal points F (i) are selected. The selected combinations are reflected in the transmitting element selector 102C and the receiving element selector 102W, respectively so that the ultrasonic transducer elements to be used for transmission and reception are restricted.

FIG. 7 shows an example of a table formed by combining the delay time table shown in FIG. 4 and the table (shown in FIG. 6) indicative of the combinations of ultrasonic transducer elements. In FIG. 7, an ON state is indicated by a positive delay time (Pik, Rik), and an OFF state is indicated by −1.

Next, an imaging operation by the ultrasonic measurement apparatus according to the present embodiment is described with reference to FIGS. 8A to 11.

Figure 9:
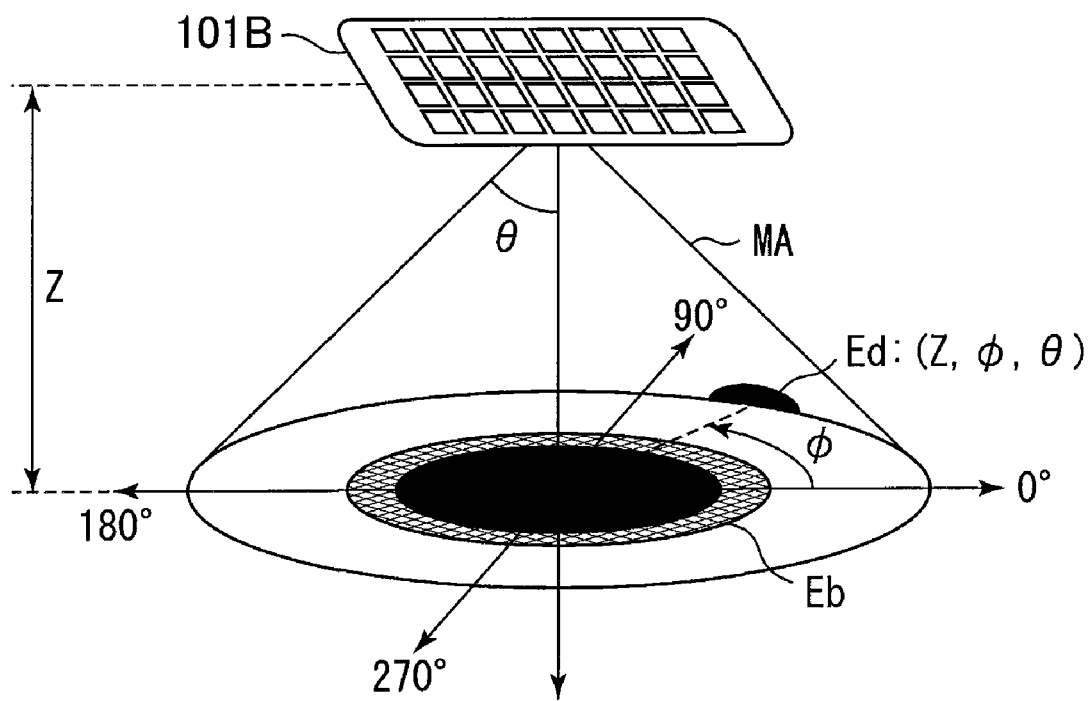
FIG. 9 is a diagram showing a region that is measured by the ultrasonic measurement apparatus according to the first embodiment of the present invention.
Figure 10A:
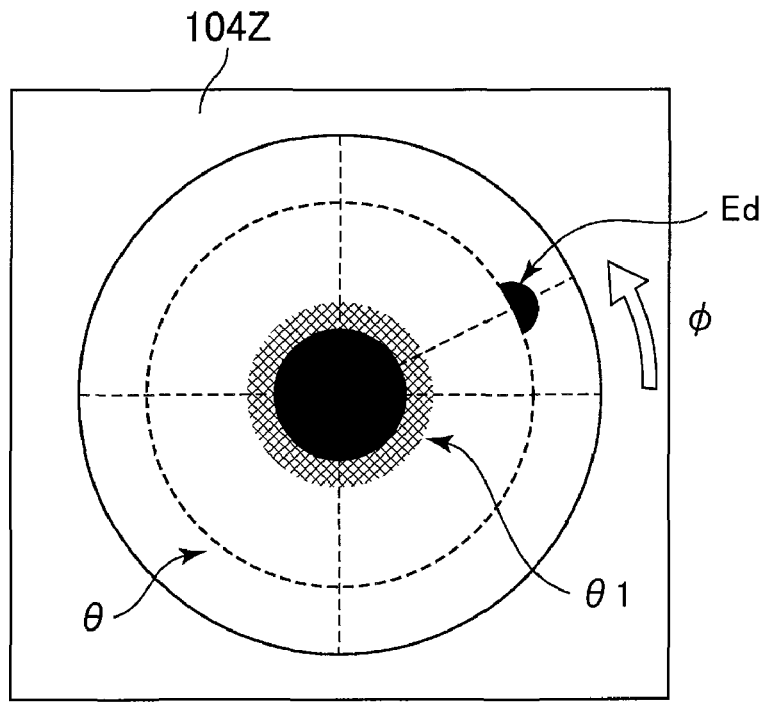
FIGS. 10A and 10B diagrams each showing an example of an image displayed by the ultrasonic measurement apparatus according to the first embodiment of the present invention.
Figure 10B:
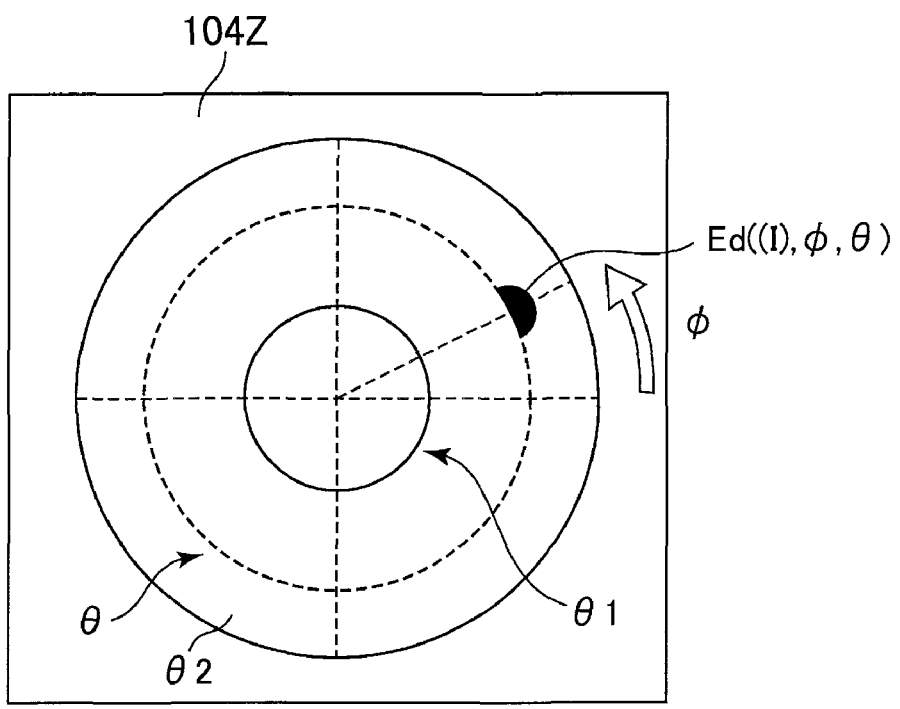
Figure 11:
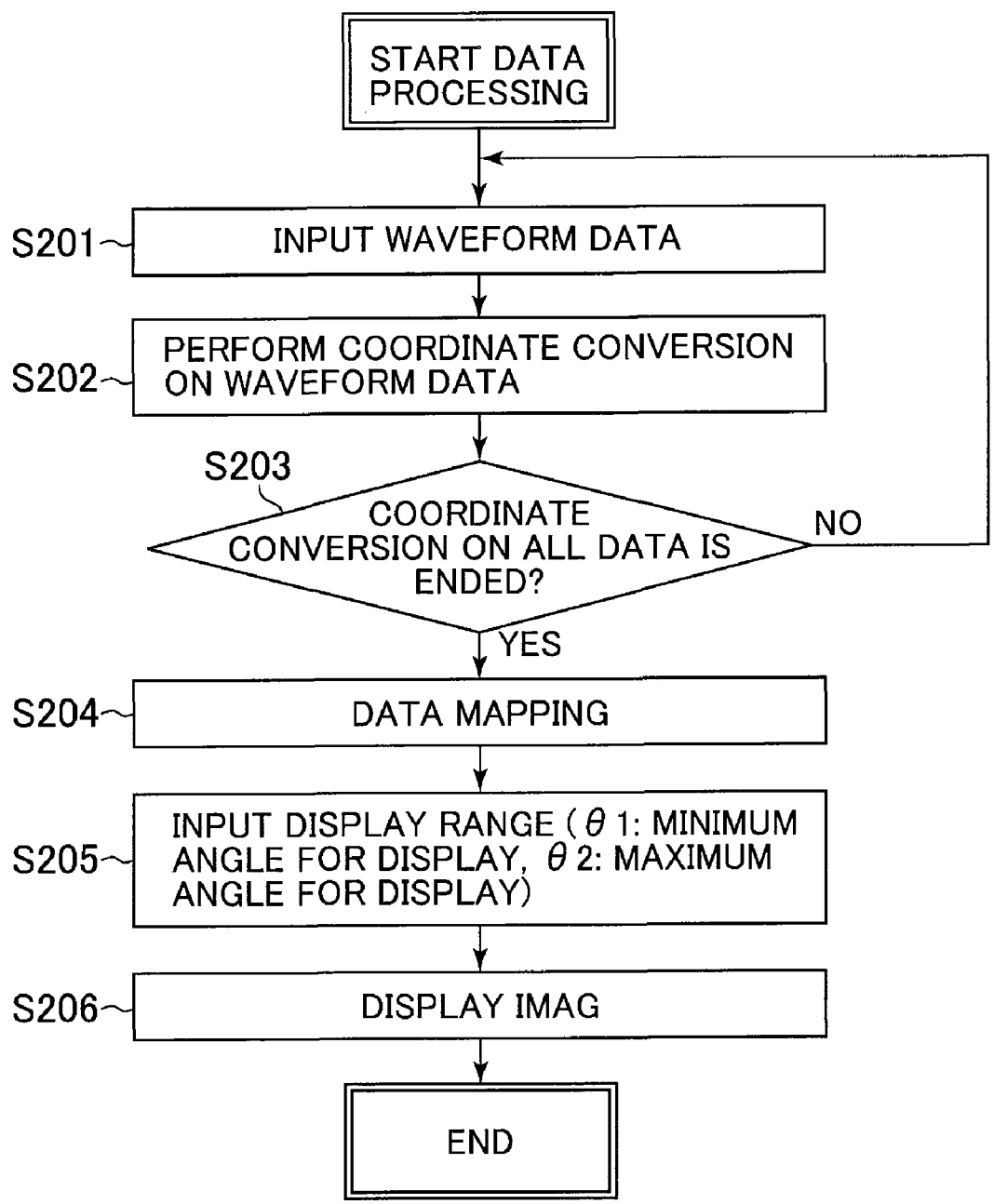
FIG. 11 is a flowchart showing content of a displaying process that is performed by the ultrasonic measurement apparatus according to the first embodiment of the present invention.
Figure 12:
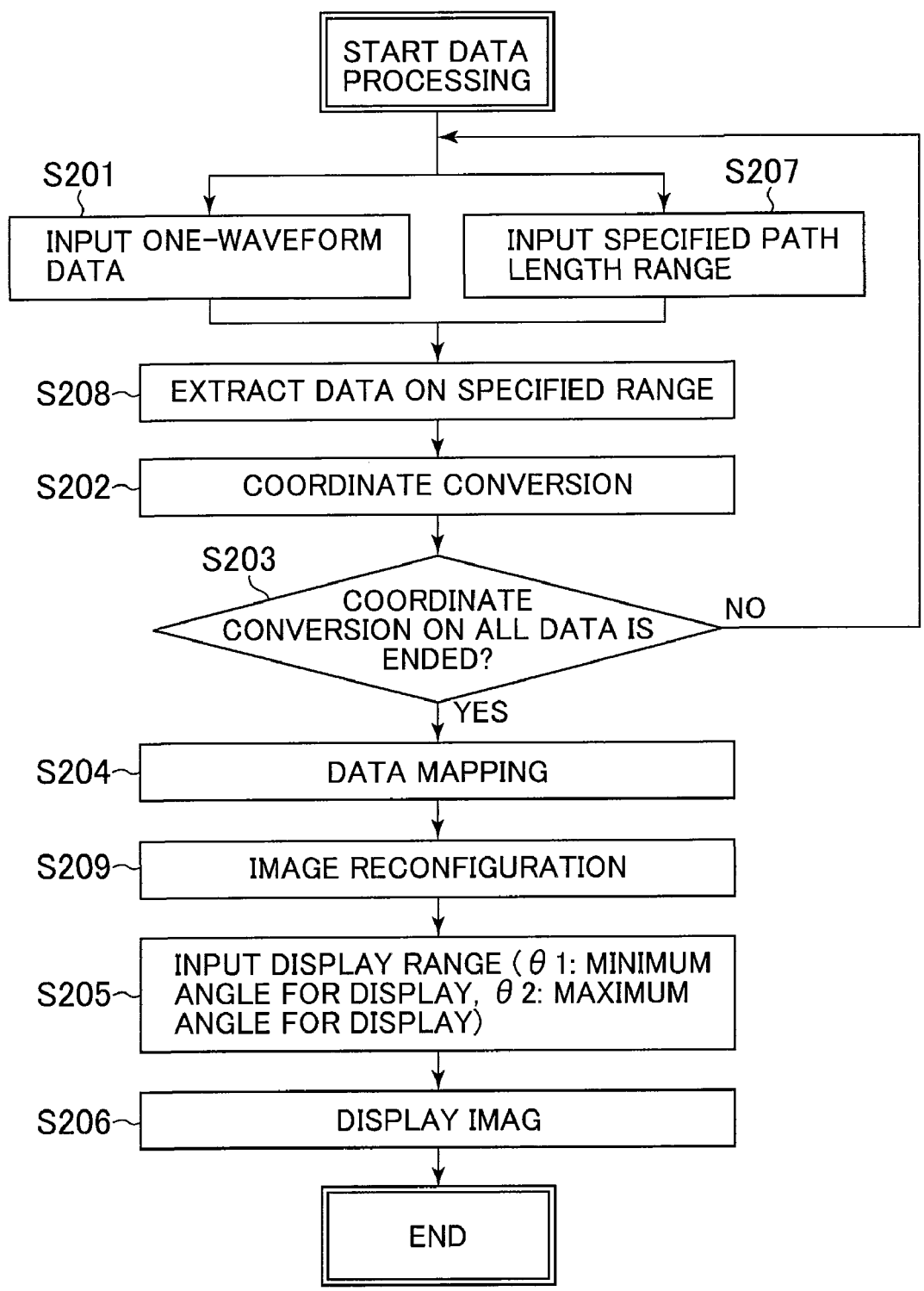
FIG. 12 is a flowchart showing other content of the displaying process that is performed by the ultrasonic measurement apparatus according to the first embodiment of the present invention.

FIGS. 8A and 8B are diagrams showing the imaging operation that is performed by the ultrasonic measurement apparatus according to the first embodiment of the present invention. FIG. 9 is a diagram showing a region to be measured by the ultrasonic measurement apparatus according to the first embodiment of the present invention. FIGS. 10A and 10B are diagrams each showing an example of an image displayed by the ultrasonic measurement apparatus according to the first embodiment of the present invention. FIG. 11 is a flowchart showing content of a displaying process that is performed by the ultrasonic measurement apparatus according to the first embodiment of the present invention. FIG. 12 is a flowchart showing other content of the displaying process that is performed by the ultrasonic measurement apparatus according to the first embodiment of the present invention.

The schematic diagram of FIG. 8A shows the state in which data D (F (i)) on the focal points F (i) set on the basis of the delay times are obtained by electronic scanning and stored. In the data D (F (i)), the abscissa represents a path length (R), and the ordinate represents the intensity (I), as shown on the upper left side of FIG. 8A.

Various signal processing such as detection processing, gain processing, and filter processing are performed on the data D (F (i)). After that, the data is converted into image data, or the data on each focal point is converted into image data. Then, interpolation processing is performed on the data so that a three-dimensional image is displayed. As a result, three-dimensional measurement results are obtained from a measured region MA shown in FIG. 9.

A three-dimensional imaging operation is performed in a three-dimensional measurement process using an ultrasonic wave and the measurement results are displayed in general. However, it takes time to perform data processing and display data. To avoid this, a method for downgrading the display method from the 3D display method to a 2D display method in the ultrasonic inspection process is described with reference to FIGS. 8A and 8B.

The sensor 101B shown in FIG. 8A transmits and receives ultrasonic waves to and from the focal points F (i) to obtain the data D (F (i)). The data D (F (i)) is regarded as data having an azimuth angle ($\phi$), a refraction angle ($\theta$), and a path length as variables for each intensity (I). The data is converted and projected onto a projective plane PL shown in FIG. 8B using the following formula.

$$I(R, \theta, \phi) \rightarrow I(R \sin \theta \cos \phi, R \sin \theta \sin \phi) \quad (1)$$

The azimuth angle ($\phi$), the refraction angle ($\theta$) and the depth (Z) are shown in FIG. 9.

In FIG. 8B, the surface 101B' of the sensor is projected onto the projective plane PL. The data D (F (i)) projected on the projective plane PL is subjected to interpolation processing in association with the intensities (I) of the data D (F (i)) projected on pixels Aij of the projective plane PL in a similar manner to an operation for displaying a sector image. As shown in FIG. 10A, the thus obtained data is displayed on the display screen 104Z shown in FIG. 1. In an example of FIG. 10A, a defect echo Ed and a bottom surface echo Eb are shown.

However, the data D (F (i)) projected on the projective plane PL may overlap depending on the method for setting the focal points, as shown in FIG. 8B. In this case, adding and average processing may be performed on each focal point.

As an ideal method, the focal points are set in a refraction angle range in which the measurement needs to be performed under the condition that the data is prevented from overlapping each other.

When the data is displayed, there is a range in which a desired signal is not returned depending on the bottom surface echo or an insensitive region. Thus, the focal points may be set outside the aforementioned range. Alternatively, the focal points may be stored, and only focal points within a specified refraction angle range may be displayed as shown in FIG. 10B. Specifically, the minimum angle $\theta 1$ for display is set, and a region that is smaller than a region defined by the minimum angle $\theta 1$ is not displayed. It should be noted that an angle $\theta 2$ is the maximum angle for display.

Next, procedures for displaying the measurement results described with reference to FIGS. 8A to 10B are described with reference to FIG. 11.

When the data processing is performed on the stored data, the control processing computer 103A receives data on one waveform from among all the stored data in step S201.

Next, coordinate conversion is performed on the one-waveform data in step S202. Then, it is determined whether or not the coordinate conversion of all the data is ended in step S203. When the coordinate conversion of all the data is not ended (or when the answer in step S203 is NO), the control processing computer 103A receives the data on the next waveform and performs data processing on the data on the next waveform.

When the coordinate conversion of all the data is ended (or when the answer in step S203 is YES), data mapping is performed in step S204. Then, a display range (refraction angle range) is specified in step S205, and an image is displayed in step S206. Then, the process is ended.

Next, other procedures for displaying the measurement results described with reference to FIGS. 8A to 10B are described with reference to FIG. 12.

When the shape of a target to be measured is known, a range of the path length of data is pre-specified so that an unwanted signal is not displayed, as described below.

When the data processing is performed on the stored data, the control processing computer 103A receives the stored data on one waveform in step S201' (S201B).

A path length range that needs to be extracted from the data on the one waveform is input in step S207.

The data on the one waveform, which corresponds to an input depth range, is extracted in step S208.

Next, coordinate conversion is performed on the one-waveform data in step S202. Then, it is determined whether or not coordinate conversion of all the data is ended in step S203. When the coordinate conversion of all the data is not ended (or when the answer in step S203 is NO), the control processing computer 103A receives the data on the next waveform and performs data processing on the data on the next waveform.

When the coordinate conversion of all the data is ended (or when the answer in step S203 is YES), data mapping is performed in step S204. The image is reconfigured in step S209. Then, a display range (refraction angle range) is specified in step S205, and the image is displayed in step S206. Then, the process is ended.

The ultrasonic measurement apparatus may have a function of displaying information on the refraction angle (θ), the azimuth angle (φ), and the intensity (I) when a cursor is placed on the image shown in FIG. 10A or 10B.

In order to obtain high resolution (for visualization) for a certain address of a signal, the image may be colored on the basis of the intensities (I) shown in the data D (F (i)).

Next, combinations of ultrasonic wave transmitting elements included in the ultrasonic measurement apparatus according to the present embodiment and combinations of ultrasonic wave receiving elements included in the ultrasonic measurement apparatus according to the present embodiment are described with reference to FIGS. 13 to 17.

Figure 13:
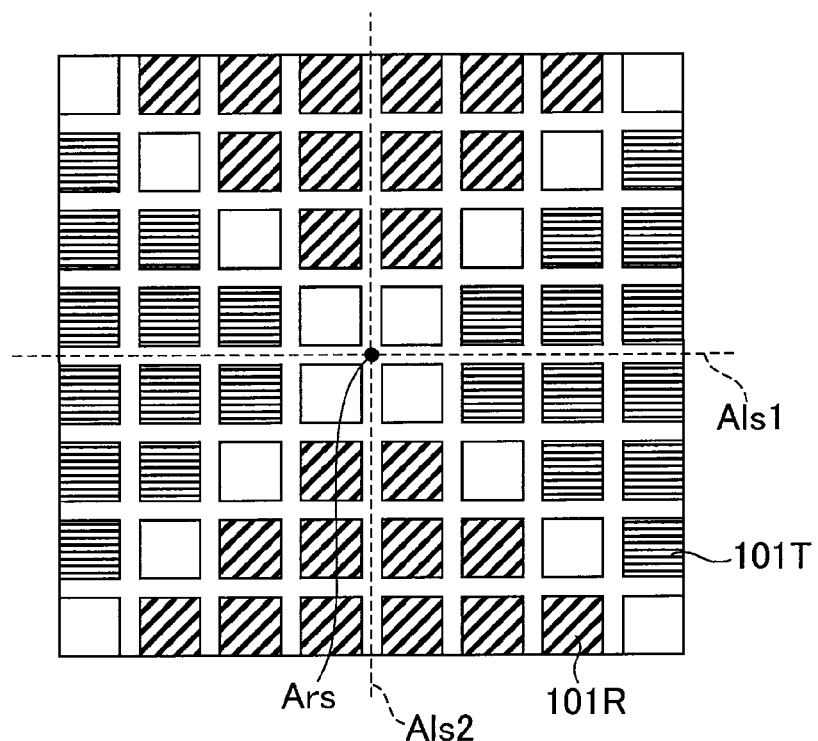
FIG. 13 is a diagram showing a first example of a combination of ultrasonic wave transmitting elements included in the ultrasonic measurement apparatus according to the first embodiment of the present invention and a combination of ultrasonic wave receiving elements included in the ultrasonic measurement apparatus according to the first embodiment of FIG. 14 is a diagram showing a second example of a combination of ultrasonic wave transmitting elements included in the ultrasonic measurement apparatus according to the first embodiment of the present invention and a combination of ultrasonic wave receiving elements included in the ultrasonic measurement apparatus according to the first embodiment of the present invention.
Figure 14:
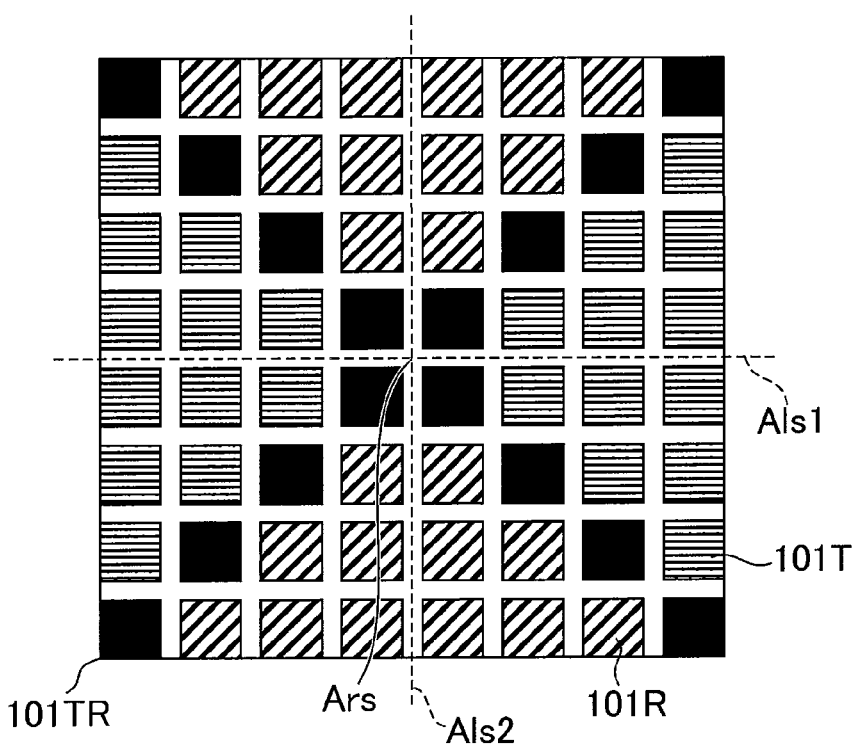
Figure 15:
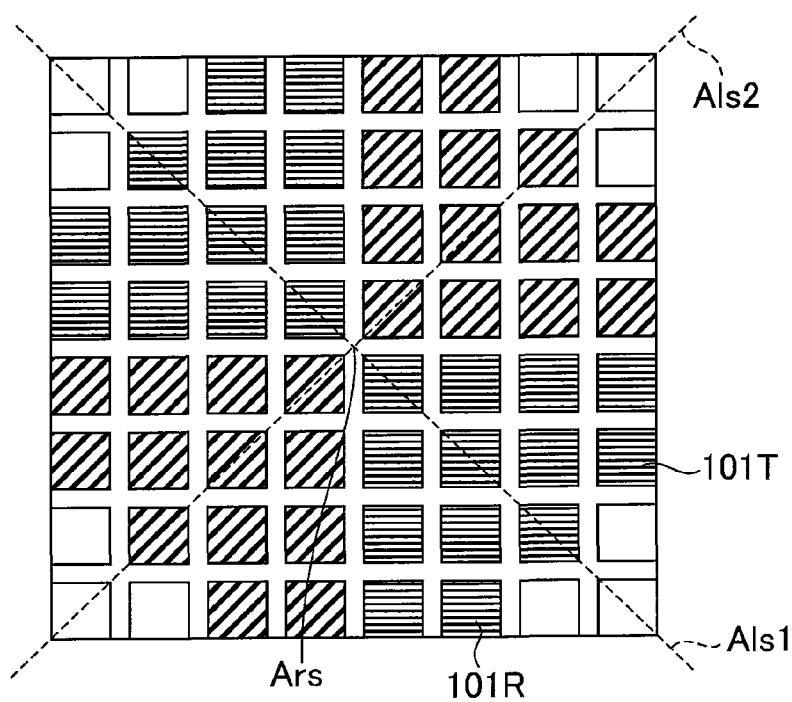
FIG. 15 is a diagram showing a third example of a combination of ultrasonic wave transmitting elements included in the ultrasonic measurement apparatus according to the first embodiment of the present invention and a combination of ultrasonic wave receiving elements included in the ultrasonic measurement apparatus according to the first embodiment of the present invention.
Figure 16:
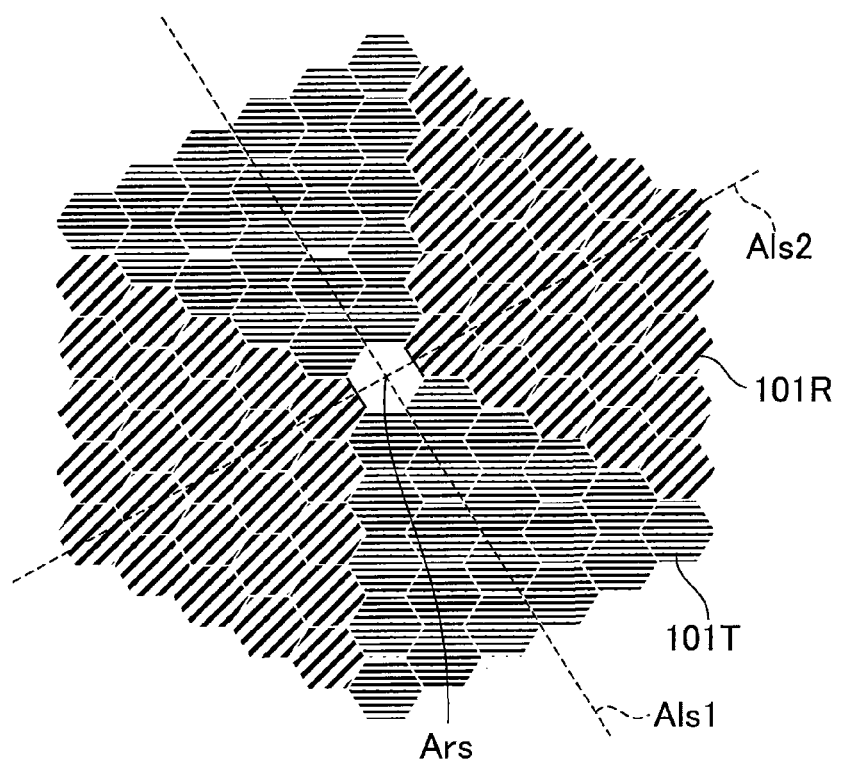
FIG. 16 is a diagram showing a fourth example of a combination of ultrasonic wave transmitting elements included in the ultrasonic measurement apparatus according to the first embodiment of the present invention and a combination of ultrasonic wave receiving elements included in the ultrasonic measurement apparatus according to the first embodiment of the present invention.
Figure 17:
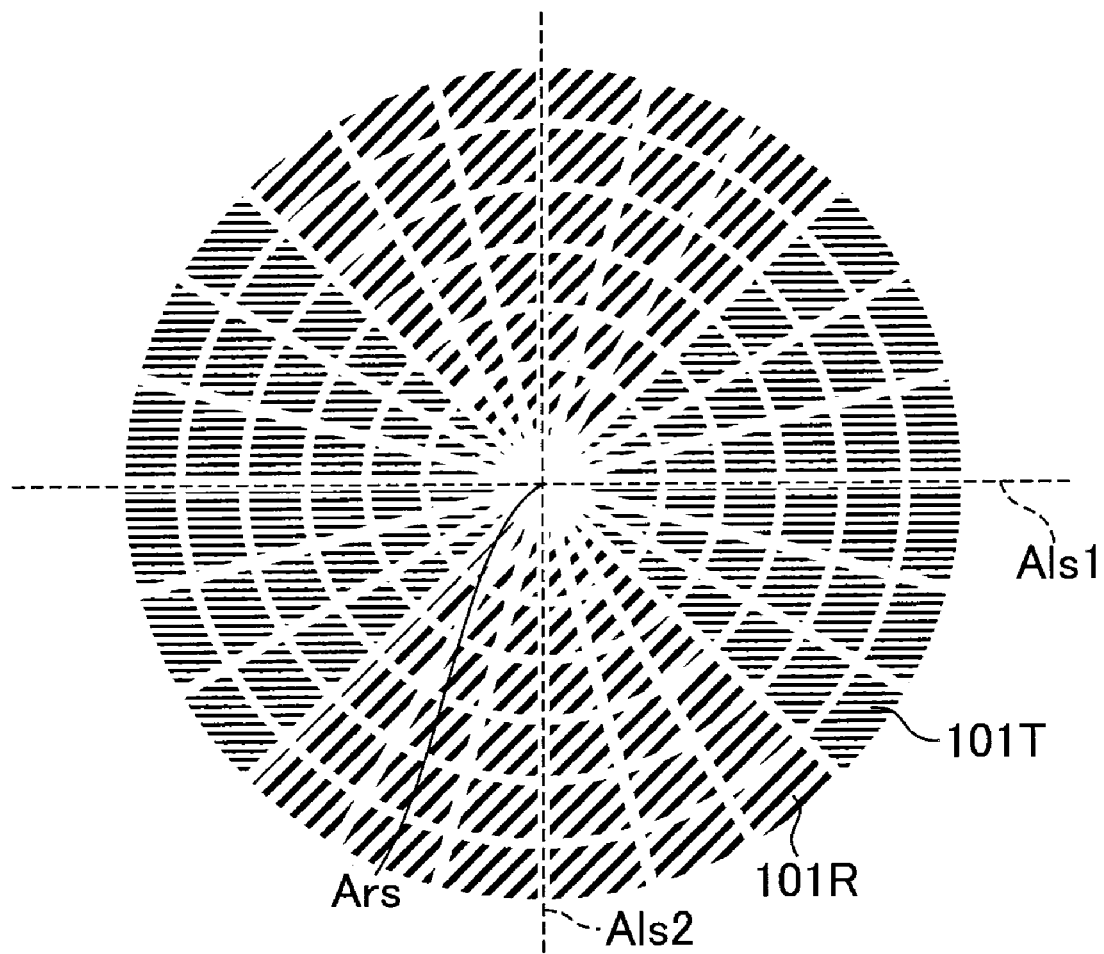
FIG. 17 is a diagram showing a fifth example of a combination of ultrasonic wave transmitting elements included in the ultrasonic measurement apparatus according to the first embodiment of the present invention and a combination of ultrasonic wave receiving elements included in the ultrasonic measurement apparatus according to the first embodiment of the present invention.

FIG. 13 is a diagram showing a first example of a combination of ultrasonic wave transmitting elements included in the ultrasonic measurement apparatus according to the first embodiment of the present invention and a combination of ultrasonic wave receiving elements included in the ultrasonic measurement apparatus according to the first embodiment of the present invention. FIG. 14 is a diagram showing a second example of a combination of ultrasonic wave transmitting elements included in the ultrasonic measurement apparatus according to the first embodiment of the present invention and a combination of ultrasonic wave receiving elements included in the ultrasonic measurement apparatus according to the first embodiment of the present invention. FIG. 15 is a diagram showing a third example of a combination of ultrasonic wave transmitting elements included in the ultrasonic measurement apparatus according to the first embodiment of the present invention and a combination of ultrasonic wave receiving elements included in the ultrasonic measurement apparatus according to the first embodiment of the present invention. FIG. 16 is a diagram showing a fourth example of a combination of ultrasonic wave transmitting elements included in the ultrasonic measurement apparatus according to the first embodiment of the present invention and a combination of ultrasonic wave receiving elements included in the ultrasonic measurement apparatus according to the first embodiment of the present invention. FIG. 17 is a diagram showing a fifth example of a combination of ultrasonic wave transmitting elements included in the ultrasonic measurement apparatus according to the first embodiment of the present invention and a combination of ultrasonic wave receiving elements included in the ultrasonic measurement apparatus according to the first embodiment of the present invention.

As described above, in the method and apparatus using the array sensor according to the present embodiment, a single reflection signal and a plurality of reflection signals are stored by means of a combination of ultrasonic wave transmitting elements and a combination of ultrasonic wave receiving elements. Thus, various combinations of ultrasonic wave transmitting elements and various combinations of ultrasonic wave receiving elements can be used. In addition, an ultrasonic wave can be transmitted in various directions and can be received from various directions.

First, the first example of the combination of the ultrasonic wave transmitting elements and the combination of the ultrasonic wave receiving elements is described below with reference to FIG. 13.

FIG. 13 shows the case in which a rectangular array sensor is used. In the first example, the array sensor is constituted by 64 ultrasonic transducer elements arranged in 8 rows and 8 columns.

The elements shown by horizontal hatching lines are selected as transmitting elements 101T, while the elements shown by oblique hatching lines are selected as receiving elements 101R.

In FIG. 13, a broken line Als1 denotes a line symmetric axis. The line symmetric axis Als1 indicates a direction specified by the azimuth angle φ shown in FIG. 9. The transmitting elements 101T are selected and arranged in line symmetry with respect to the line symmetric axis Als1. In addition, adjacent elements are selected as the transmitting elements 101T from the plurality of elements.

A broken line Als2 denotes a line symmetric axis that is perpendicular to the line symmetric axis Als1 and passes through a rotationally symmetric axis Ars. The line symmetric axis Als2 indicates a direction specified by an angle obtained by adding 180 degrees to the azimuth angle φ shown in FIG. 9. The receiving elements 101R are selected and arranged in line symmetry with respect to the line symmetric axis Als2. In addition, adjacent elements are selected as the receiving elements 101R from the plurality of elements. Elements denoted by white squares are not used for both transmission and reception.

In this case, the receiving elements 101R and the transmitting elements 101T are selected and arranged in rotational symmetry about the rotationally symmetric axis Ars that extends in the direction perpendicular to the surface of the paper of FIG. 13.

Next, the second example of the combination of ultrasonic wave transmitting elements and the combination of ultrasonic wave receiving elements is described with reference to FIG. 14.

FIG. 14 shows the case in which a rectangular array sensor is used. In the second example, the array sensor is constituted by 30 ultrasonic transducer elements arranged in 6 rows and 6 columns.

The elements shown by horizontal hatching lines are selected as transmitting elements 101T, while the elements shown by oblique hatching lines are selected as receiving elements 101R. Elements denoted by black squares are selected as transmitting/receiving elements 101TR that are used to transmit and receive an ultrasonic wave.

In FIG. 14, a broken line Als1 denotes a line symmetric axis. The line symmetric axis Als1 indicates the direction specified by the azimuth angle φ shown in FIG. 9. The transmitting elements 101T are selected and arranged in line symmetry with respect to the line symmetric axis Als1. In addition, adjacent elements are selected as the transmitting elements 101T from the plurality of elements.

A broken line Als2 denotes a line symmetric axis that is perpendicular to the line symmetric axis Als1 and passes through a rotationally symmetric axis Ars. The line symmetric axis Als2 indicates the direction specified by the angle obtained by adding 180 degrees to the azimuth angle φ shown in FIG. 9. The receiving elements 101R are selected and arranged in line symmetry with respect to the line symmetric axis Als2. In addition, adjacent elements are selected as the receiving elements 101R from the plurality of elements.

The elements shown by the black squares are the transmitting/receiving elements 101TR that are used for transmission and reception. In the example shown in FIG. 13, the elements arranged on the diagonals are not used for both transmission and reception. On the other hand, in the second example, the elements arranged on the diagonals are used for both transmission and reception.

In this case, the receiving elements 101R, the transmitting elements 101T, and the transmitting/receiving elements 101TR are selected and arranged in rotational symmetry about the rotationally symmetric axis Ars that extends in the direction perpendicular to the surface of the paper of FIG. 14.

Next, the third example of the combination of transmitting elements and the combination of receiving elements is described with reference to FIG. 15.

FIG. 15 shows the case in which a rectangular array sensor is used. In the third example, the array sensor is constituted by 30 ultrasonic transducer elements arranged in 6 rows and 6 columns.

The elements shown by horizontal hatching lines are selected as transmitting elements 101T, while the elements shown by oblique hatching lines are selected as receiving elements 101R.

In FIG. 15, a broken line Als1 is a diagonal and denotes a line symmetric axis. The line symmetric axis Als1 indicates the direction specified by the azimuth angle φ shown in FIG. 9. The transmitting elements 101T are selected and arranged in line symmetry with respect to the line symmetric axis Als1. In addition, adjacent elements are selected as the transmitting elements 101T from the plurality of elements.

A broken line Als2 is a diagonal and denotes a line symmetric axis that is perpendicular to the line symmetric axis Als1 and passes through a rotationally symmetric axis Ars. The line symmetric axis Als2 indicates the direction specified by the angle obtained by adding 180 degrees to the azimuth angle φ shown in FIG. 9. The receiving elements 101R are selected and arranged in line symmetry with respect to the line symmetric axis Als2. In addition, adjacent elements are selected as the receiving elements 101R from the plurality of elements. Elements denoted by white squares are not used for both transmission and reception.

In this case, the receiving elements 101R and the transmitting elements 101T are selected and arranged in rotational symmetry about the rotationally symmetric axis Ars that extends in the direction perpendicular to the surface of the paper of FIG. 15.

Next, the fourth example of the combination of ultrasonic wave transmitting elements and the combination of ultrasonic wave receiving elements is described with reference to FIG. 16.

FIG. 16 shows the case in which an array sensor having ultrasonic transducer elements arranged in a hexagonal shape is used. In the fourth example, six ultrasonic transducer elements are arranged on one side of the outermost circumference, while the number of ultrasonic transducer elements is smaller toward the inner circumference side. The array sensor shown in FIG. 16 is constituted by 91 ultrasonic transducer elements.

The elements shown by horizontal hatching lines are selected as transmitting elements 101T, while the elements shown by oblique hatching lines are selected as receiving elements 101R.

In FIG. 16, a broken line Als1 denotes a line symmetric axis. The line symmetric axis Als1 indicates the direction specified by the azimuth angle φ shown in FIG. 9. The transmitting elements 101T are selected and arranged in line symmetry with respect to the line symmetric axis Als1. In addition, adjacent elements are selected as the transmitting elements 101T from the plurality of elements.

A broken line Als2 denotes a line symmetric axis that is perpendicular to the line symmetric axis Als1 and passes through a rotationally symmetric axis Ars. The line symmetric axis Als2 indicates the direction specified by the angle obtained by adding 180 degrees to the azimuth angle φ shown in FIG. 9. The receiving elements 101R are selected and arranged in line symmetry with respect to the line symmetric axis Als2. In addition, adjacent elements are selected as the receiving elements 101R from the plurality of elements. An element denoted by a white hexagon is not used for both transmission and reception.

In this case, the receiving elements 101R and the transmitting elements 101T are selected and arranged in rotational symmetry about the rotationally symmetric axis Ars that extends in the direction perpendicular to the surface of the paper of FIG. 16.

Next, the fifth example of the combination of ultrasonic wave transmitting elements and the combination of ultrasonic wave receiving elements is described with reference to FIG. 17.

FIG. 17 shows the case in which an array sensor having ultrasonic transducer elements arranged in a circular shape is used. In the fifth example, the array sensor is constituted by 121 ultrasonic transducer elements while 24 ultrasonic transducer elements are arranged in a circumferential direction of the sensor.

The elements shown by horizontal hatching lines are selected as transmitting elements 101T, while the elements shown by oblique hatching lines are selected as receiving elements 101R.

In FIG. 17, a broken line Als1 denotes a line symmetric axis. The line symmetric axis Als1 indicates the direction specified by the azimuth angle φ shown in FIG. 9. The transmitting elements 101T are selected and arranged in line symmetry with respect to the line symmetric axis Als1. In addition, adjacent elements are selected as the transmitting elements 101T from the plurality of elements.

A broken line Als2 denotes a line symmetric axis that is perpendicular to the line symmetric axis Als1 and passes through a rotationally symmetric axis Ars. The line symmetric axis Als2 indicates the direction specified by the angle obtained by adding 180 degrees to the azimuth angle φ shown in FIG. 9. The receiving elements 101R are selected and arranged in line symmetry with respect to the line symmetric axis Als2. In addition, adjacent elements are selected as the receiving elements 101R from the plurality of elements. An element that is denoted by a white circle and is located at a central portion of the sensor is not used for both transmission and reception.

In this case, the receiving elements 101R and the transmitting elements 101T are selected and arranged in rotational symmetry about the rotationally symmetric axis Ars that extends in the direction perpendicular to the surface of the paper of FIG. 17.

In the present embodiment, as described above, the array sensor is capable of transmitting and receiving an ultrasonic wave while maintaining a point focusing effect in a certain refraction angle range selected from among a range of 0 to 90 degrees with respect to a normal without performing mechanical scanning in all directions.

Next, the configuration and operations of an ultrasonic measurement apparatus according to a second embodiment of the present invention are described with reference to FIGS. 18 to 20.

First, the entire configuration of the ultrasonic measurement apparatus according to the second embodiment is described with reference to FIG. 18.

Figure 18:
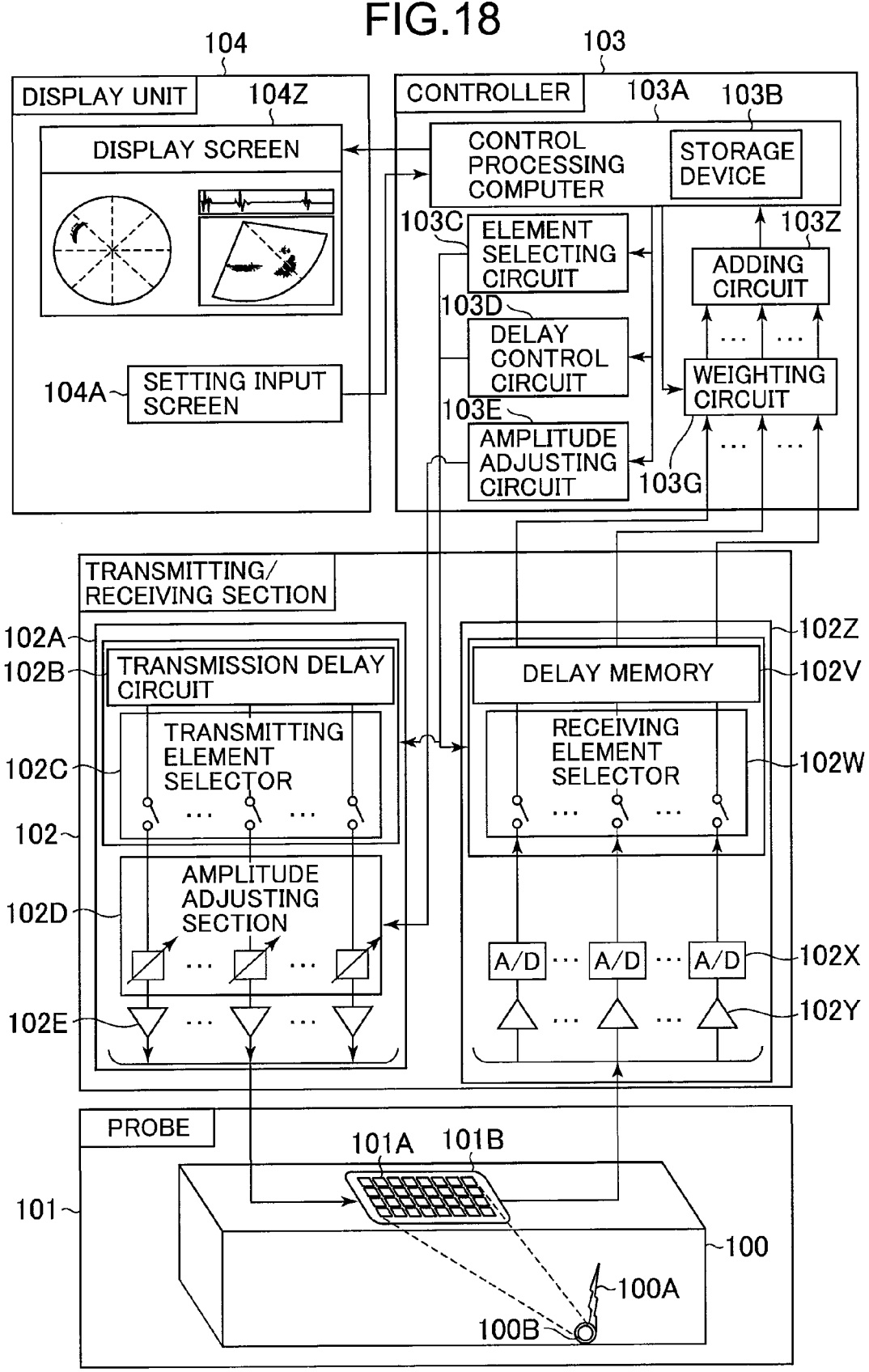
FIG. 18 is a block diagram showing the entire configuration of an ultrasonic measurement apparatus according to a second embodiment of the present invention.

FIG. 18 is a block diagram showing the entire configuration of the ultrasonic measurement apparatus according to the second embodiment of the present invention.

When such an array sensor as shown in FIG. 17 is used, the sizes of the elements that constitute the array sensor vary. Thus, the intensities of ultrasonic waves transmitted by the elements vary, and receiving sensitivity of the elements varies. To avoid this, an ultrasonic wave to be received is weighted by the apparatus (shown in FIG. 18) according to the present embodiment so that the intensity of the ultrasonic wave to be transmitted by each element or receiving sensitivity of each element is calibrated to reduce the variation in the sensitivity.

The ultrasonic measurement apparatus according to the present embodiment measures the object 100 and the reflection source 100A located inside the object or on the surface of the object with an excellent SN ratio, for example. The ultrasonic measurement apparatus according to the present embodiment includes a probe 101, a transmitting/receiving section 102, a controller 103, and a display unit 104.

The transmitting/receiving section 102 includes an amplitude adjusting section 102D in addition to the configuration shown in FIG. 1. The amplitude adjusting section 102D finely adjusts the intensity of an ultrasonic wave that is to be transmitted by each element that constitutes the array sensor. The controller 103 includes a weighting circuit 103G that weights the receiving sensitivity of each element.

If it is difficult that the amplitude adjusting section 102D adjusts the intensity of an ultrasonic wave (that is to be transmitted by each element) for a technical reason and the amplitude adjusting section 102D cannot be installed in the apparatus, the weighting circuit 103G may weight only waveform data on received ultrasonic waves.

The weighting circuit 103G adjusts a waveform of a received signal having a delay time added thereto in a similar manner to the amplitude adjusting section 102D. The weighting circuit 103G has weighting constants W1 to Wn for the respective elements and multiplies signals output from the elements by the respective weighting constants W1 to Wn.

Next, a method for determining the weighting constants W1 to Wn is described with reference to FIGS. 19 and 20.

Figure 19:
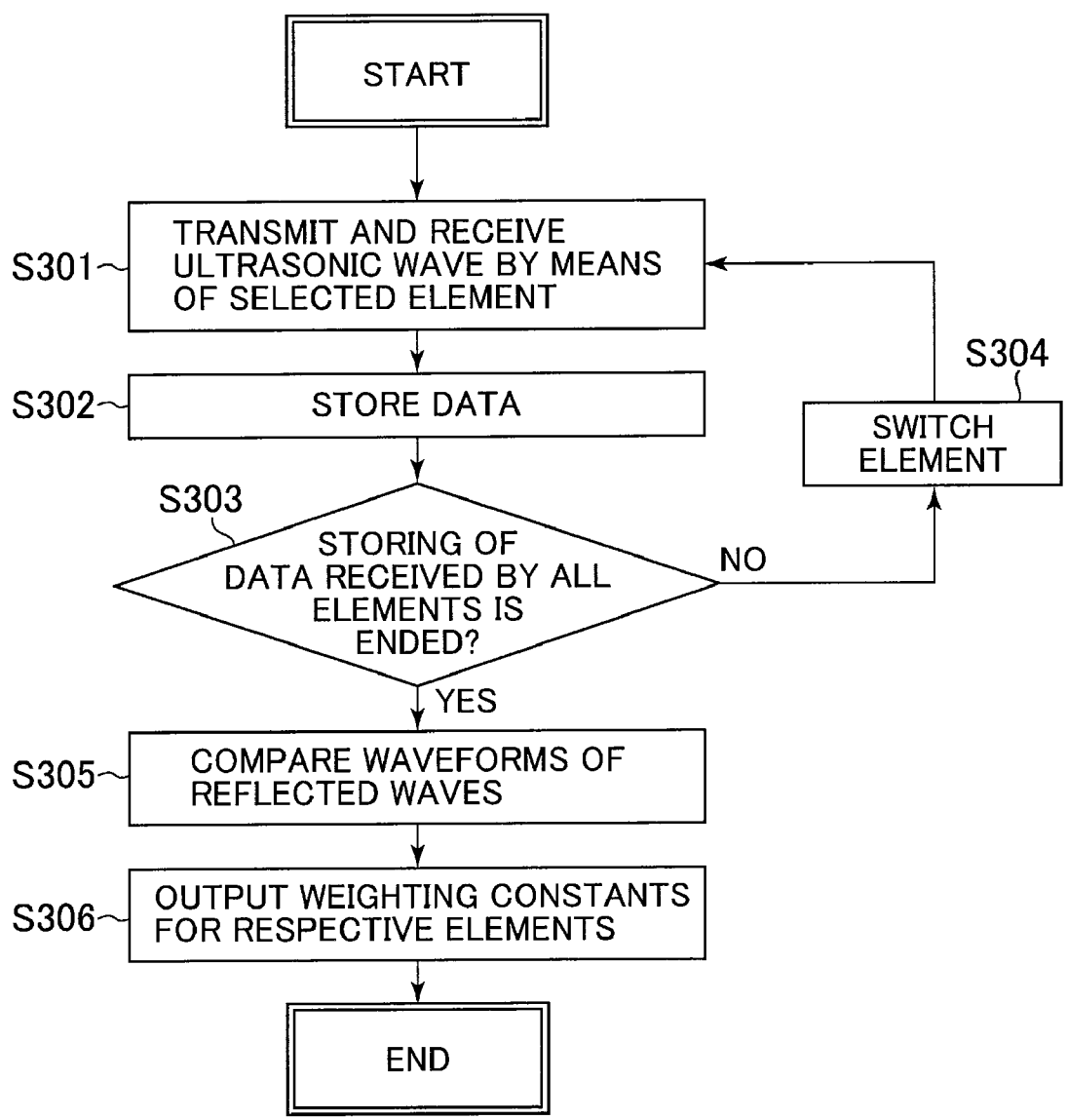
FIG. 19 is a flowchart showing content of a method for determining a weighting constant for the ultrasonic measurement apparatus according to the second embodiment of the present invention.
Figure 20:
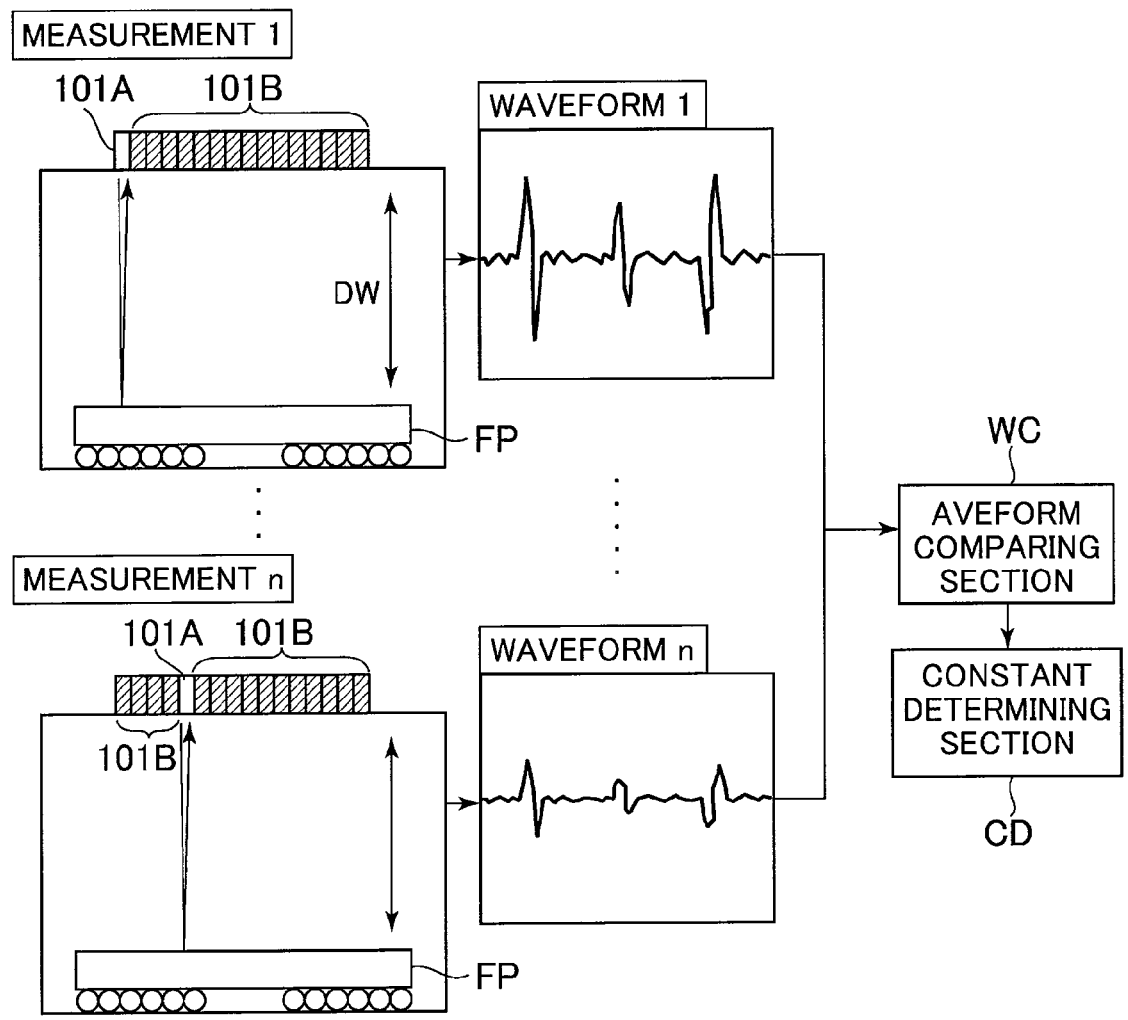
FIG. 20 a flowchart showing content of a method for determining a weighting constant for the ultrasonic measurement apparatus according to the second embodiment of the present invention.

FIG. 19 is a flowchart showing content of the method for determining the weighting constants for the ultrasonic measurement apparatus according to the present embodiment. FIG. 20 is an explanatory diagram showing the content of the method for determining the weighting constants for the ultrasonic measurement apparatus according to the present embodiment.

In order to determine an N number of the weighting constants W1 to Wn for the elements (it is assumed that the number of the elements is N), the elements 101A (sensor illustrated in white in FIG. 20) that constitute the array sensor 101B each transmit and receive an ultrasonic wave sequentially to and from a flat plate FP that is located in water and has a surface parallel to the surface of the sensor 101B so that reflection data that is obtained from waves reflected from the surface of the flat plate FP is stored.

A waveform comparing section WC compares values of the reflection data stored for each element. A constant determining section CD determines the weighting constants W1 to Wn (for the respective elements) for calibration so that the heights of the reflected waves received by all the elements are the same.

The content of a process for determining the weighting constants is described with reference to FIG. 19.

First, the elements 101A that constitute the array sensor 101B each transmit and receive an ultrasonic wave in step S301, as described with reference to FIG. 20, and data is stored in step S302.

Then, it is determined that data received by all the elements is stored in step S303. When the storing is not ended, the element is switched in step S304 and the process returns to step S301. Until the storing of the data received by all the elements is ended, steps 301 and 302 are repeated.

After the storing is ended, the waveform comparing section WC compares wave heights of the stored data. Then, the constant determining section CD outputs weighting values for the respective elements. Then, the process is ended.

The weighting circuit 103G (shown in FIG. 18) multiplies the weighting constants W1 to Wn by the intensities of waveforms 1 to n so as to reduce a variation in the intensities of the ultrasonic waves transmitted and received by the respective elements.

The weighting constants for all the elements may be determined. When the intensities of ultrasonic waves transmitted by the elements that constitute the circular array sensor shown in FIG. 17 and are concentrically arranged vary and sensitivity of the elements varies, this method is used to perform calibration and effective in order to reduce the variation in the sensitivity in the process for inspecting an object in all directions.

In the present embodiment, the array sensor is capable of transmitting and receiving an ultrasonic wave while maintaining the point focusing effect in a certain refraction angle range selected from among a range of 0 to 90 degrees with respect to a normal without performing mechanical scanning in all directions.

In addition, it is possible to detect a defect for a short time with an excellent SN ratio while suppressing a variation (in the circumferential direction of the sensor) in sensitivity of the sensor that receives ultrasonic waves from a surface perpendicular to the normal to the facing surface of the sensor.

Next, the configuration and operations of an ultrasonic measurement apparatus according to a third embodiment of the present invention are described with reference to FIGS. 21 and 22. The entire configuration of the ultrasonic measurement apparatus according to the present embodiment is the same as the configuration shown in FIG. 1 or 18. When the elements that are used for transmission and reception are set as shown in FIG. 13, 14, 15 or 16, the ultrasonic measurement apparatus shown in FIG. 1 can be used. When the elements that are used for transmission and reception are set as shown in FIG. 17, the ultrasonic measurement apparatus shown in FIG. 18 can be used.

Figure 21:
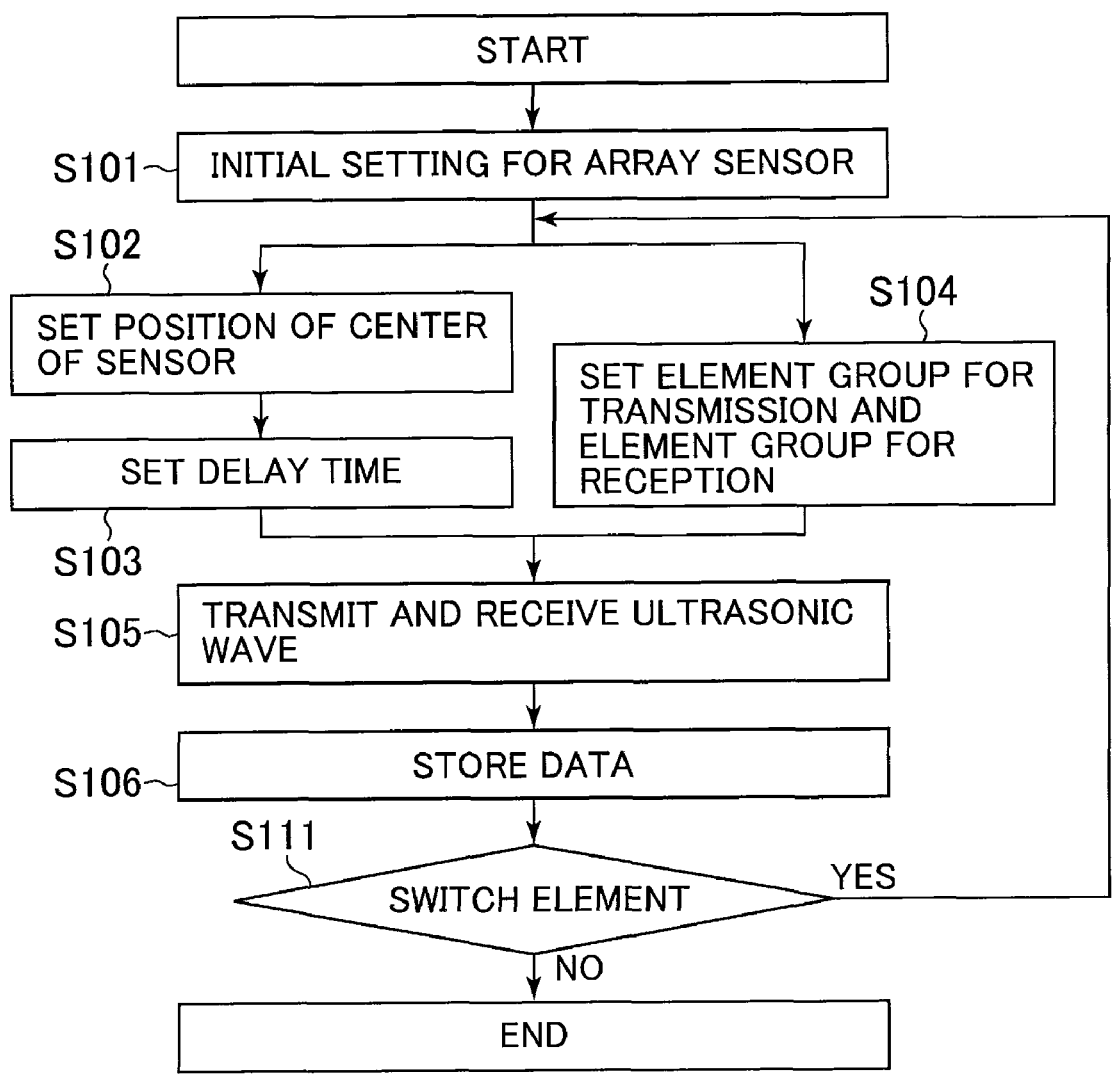
FIG. 21 is a flowchart of a method for selecting a transmitting element and a receiving element from among ultrasonic transducer elements included in an ultrasonic measurement apparatus according to a third embodiment of the present invention.

FIG. 21 is a flowchart of a method for selecting a transmitting element and a receiving element from among the elements included in the ultrasonic measurement apparatus according to the present embodiment. FIG. 22 is a diagram showing the selected transmitting and receiving elements that are included in the ultrasonic measurement apparatus according to the present embodiment.

In the present embodiment, ultrasonic transducer elements that are used for transmission and reception can be switched.

Figure 22:
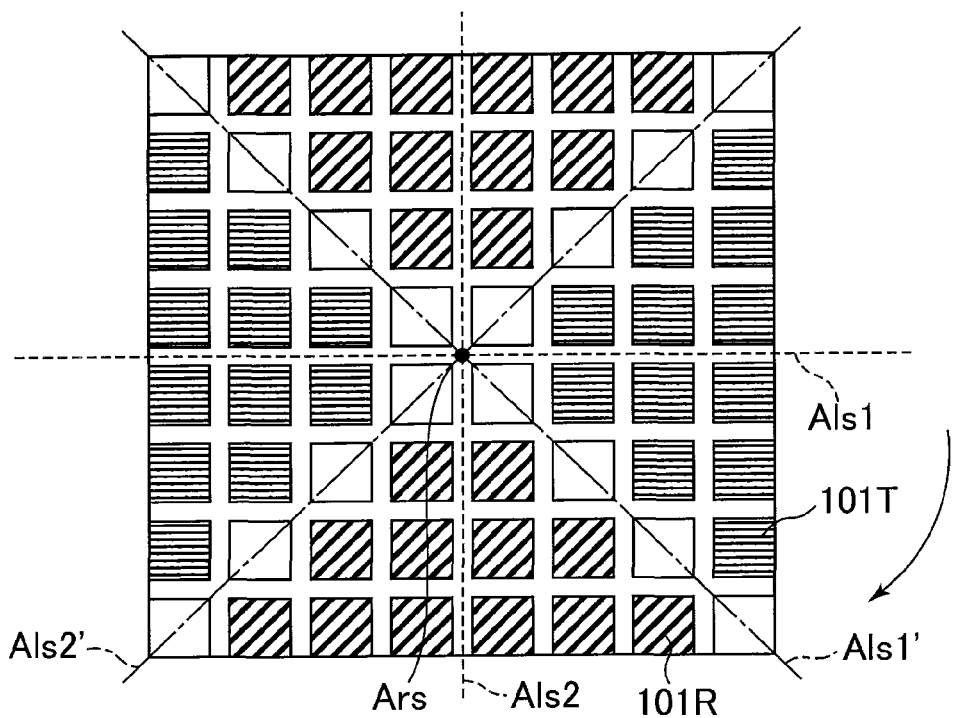
FIG. 22 is a diagram showing the selected transmitting and receiving elements that are included in the ultrasonic measurement apparatus according to the third embodiment of the present invention.

FIG. 22 is basically the same as FIG. 13. As described with reference to FIG. 13, the transmitting elements 101T are selected and arranged in line symmetry with respect to the line symmetric axis Als1. In addition, adjacent elements are selected as the transmitting elements 101T from the plurality of elements. The receiving elements 101R are selected and arranged in line symmetry with respect to the line symmetric axis Als2 that is perpendicular to the line symmetric axis Als1 and passes through the rotationally symmetric axis Ars. In addition, adjacent elements are selected as the receiving elements 101R from the plurality of elements.

When the transmitting and receiving elements are set, the elements transmit and receive ultrasonic waves in a single direction (inspection direction). Thus, receiving sensitivity of the sensor may be reduced depending on the shape of a defect or the direction in which the defect extends. In this case, when the inspection direction is changed, the receiving sensitivity can be improved.

In the present embodiment, ultrasonic transducer elements that are used for transmission and reception can be switched in order to change the inspection direction. Specifically, the line symmetric axis Als1 shown in FIG. 22 extends along a line symmetric axis Als1' by rotating about the rotationally symmetric axis Ars toward a direction indicated by an arrow shown in FIG. 22 by 45 degrees. The line symmetric axis Als2 shown in FIG. 22 extends along a line symmetric axis Als2' by rotating about the rotationally symmetric axis Ars toward the direction indicated by the arrow shown in FIG. 22 by 45 degrees. The axes Als1' and Als2' are the same as the line symmetric axes Als1 and Als2 shown in FIG. 15, respectively. Thus, the inspection direction can be changed by selecting transmitting elements 101T and receiving elements 101R as described with reference to FIG. 15.

After transmitting elements and the receiving elements are set and arranged in line symmetry with respect to the line symmetric axes, and perform an inspection, the line symmetric axes are rotated as described above. Then, transmitting elements and receiving elements are set and arranged in line symmetry with respect to the new line symmetric axes, and perform an inspection. Thus, inspections can be performed in a plurality of directions.

When transmitting elements, receiving elements, and transmitting/receiving elements are arranged as shown in FIG. 14, the line symmetric axes are rotated by 45 degrees and thereby extend along new line symmetric axes, and transmitting elements, receiving elements and transmitting/receiving elements are set and arranged in line symmetry with respect to the new line symmetric axes. Thus, an inspection can be performed in a different direction.

When the transmitting elements and the receiving elements are arranged as shown in FIG. 16, the line symmetric axes are rotated by 60 degrees and 120 degrees and thereby extend along new line symmetric axes, and transmitting elements and receiving elements are set and arranged in line symmetry with respect to the new line symmetric axes. Thus, an inspection can be performed in a different direction. In addition, when the transmitting elements and the receiving elements are arranged as shown in FIG. 16, the line symmetric axes are rotated by 30 degrees and thereby extend along new line symmetric axes, and transmitting elements and receiving elements can be set and arranged in line symmetry with respect to the new line symmetric axes.

Furthermore, when the transmitting elements and the receiving elements are arranged as shown in FIG. 17, the line symmetric axes are rotated by 15 degrees and 30 degrees and thereby extend along new line symmetric axes, and transmitting elements and receiving elements are set and arranged in line symmetry with respect to the new line symmetric axes. Thus, an inspection can be performed in a different direction. In addition, when the transmitting elements and the receiving elements are arranged as shown in FIG. 17, the line symmetric axes are rotated by 7.5 degrees and thereby extend along new line symmetric axes, and transmitting elements and receiving elements can be set and arranged in line symmetry with respect to the new line symmetric axes.

Next, a method for performing an inspection while switching transmitting and receiving elements is described with reference to FIG. 21.

When the setting is started, the inspector uses the setting input screen 104A (shown in FIG. 1) to enter, as initial settings for the array sensor, necessary information such as information on the ultrasonic transducer elements that constitute the array sensor and the velocity of an ultrasonic wave in step S101.

Then, the position of the center of the sensor having the N number of ultrasonic transducer elements, which is a reference of the delay time and image display, is set in step S102. In general, the center (intersection of a central line Cy and a central line Cx) of the ultrasonic transducer elements is set as the center C of the sensor.

Next, the control processing computer 103A calculates a pattern of delay times for the respective ultrasonic transducer elements that are included in the array sensor in step S103.

Meanwhile, the element selecting circuit 103C uses the information provided in the initial setting of step S101 to set an ultrasonic transducer element group that is to be used for transmission and reception in step S104.

The transmitting/receiving section 102 transmits and receives an ultrasonic wave on the basis of these settings in step S105, and data is stored in step S106.

Next, it is determined whether or not an operation for switching an element is ended in step S111. When the switching operation is not ended in step S111, the process returns to step S104 and new transmitting and receiving elements are set. Then, each of the set transmitting and receiving elements transmits and receives an ultrasonic wave on the basis of the settings (performed in steps S102 to S104) in step S105, and data is stored in step S106.

In the present embodiment, the array sensor is capable of transmitting and receiving an ultrasonic wave while maintaining the point focusing effect in a certain refraction angle range selected from among a range of 0 to 90 degrees with respect to a normal without performing mechanical scanning in all directions.

In addition, an SN ratio can be improved by reducing noise that is caused by a bottom surface echo.

Next, the configuration and operations of an ultrasonic measurement apparatus according to a fourth embodiment of the present invention are described with reference to FIG. 23. The entire configuration of the ultrasonic measurement apparatus according to the fourth embodiment is the same as the configuration shown in FIG. 18.

Figure 23:
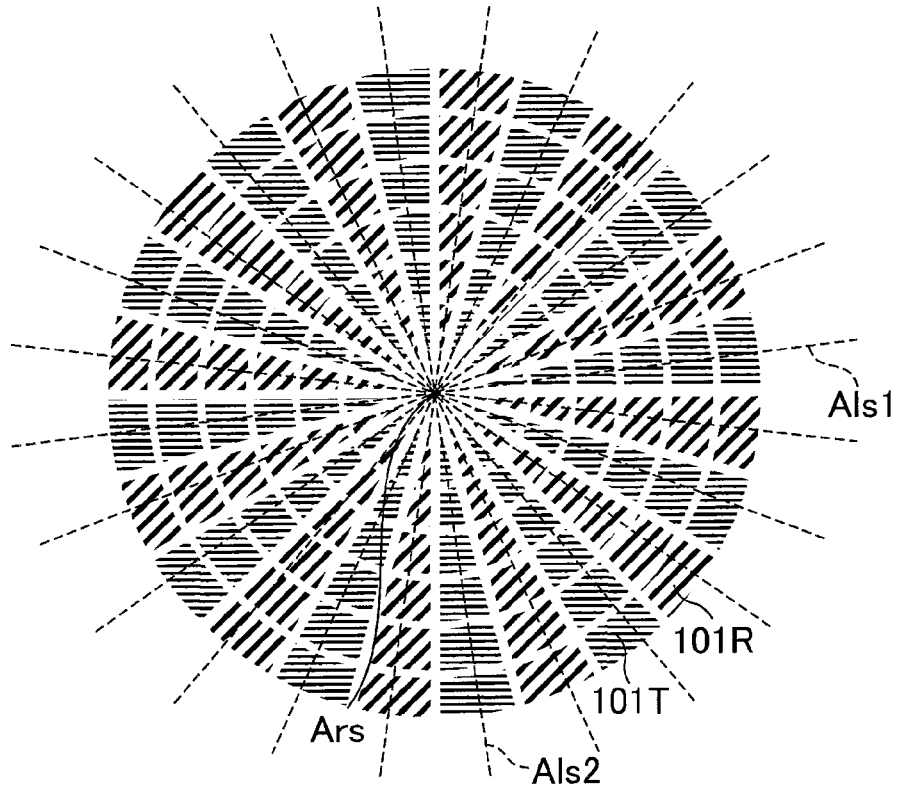
FIG. 23 is a diagram showing selected transmitting elements and selected receiving elements that are included in an ultrasonic measurement apparatus according to a fourth embodiment of the present invention.

FIG. 23 is a diagram showing transmitting and receiving elements selected from the elements included in the ultrasonic measurement apparatus according to the fourth embodiment of the present invention.

FIG. 23 shows the case in which an array sensor having ultrasonic transducer elements arranged in a circular shape (in a similar manner to the array sensor shown in FIG. 17) is used. In this example, the array sensor is constituted by 121 ultrasonic transducer elements while 24 ultrasonic transducer elements are arranged in a circumferential direction of the sensor.

The elements shown by horizontal hatching lines are selected as transmitting elements 101T, while the elements shown by oblique hatching lines are selected as receiving elements 101R.

In FIG. 23, a broken line Als1 denotes a line symmetric axis. The line symmetric axis Als1 indicates the direction specified by the azimuth angle φ shown in FIG. 9. The transmitting elements 101T are selected and arranged in line symmetry with respect to the line symmetric axis Als1. In addition, adjacent elements are selected as the transmitting elements 101T from the plurality of elements.

A broken line Als2 denotes a line symmetric axis that is perpendicular to the line symmetric axis Als1 and passes through a rotationally symmetric axis Ars. The line symmetric axis Als2 indicates the direction specified by the angle obtained by adding 180 degrees to the azimuth angle φ shown in FIG. 9. The receiving elements 101R are selected and arranged in line symmetry with respect to the line symmetric axis Als2. In addition, adjacent elements are selected as the receiving elements 101R from the plurality of elements.

In the present embodiment, the transmitting elements and the receiving elements are alternately arranged in the circumferential direction of the sensor. This feature is different from the arrangement shown in FIG. 17.

In this case, the receiving elements 101R and the transmitting elements 101T are selected and arranged in rotational symmetry about the rotationally symmetric axis Ars that extends in the direction perpendicular to the surface of the paper of FIG. 23.

All broken lines shown in FIG. 23 pass through the rotationally symmetric axis Ars and denote line symmetric axes. Transmitting elements and receiving elements can be selected and arranged in line symmetry with respect to the line symmetric axes. That is, when the segmented elements are arranged as shown in FIG. 23, the line symmetric axes sufficiently exist. Thus, when focal points are set on the line symmetric axes, it is not necessary to switch elements. Therefore, it is possible to reduce noise that is caused by a bottom surface echo and improve an SN ratio.

Next, the configuration and operations of an ultrasonic measurement apparatus according to a fifth embodiment of the present invention are described.

Figure 24:
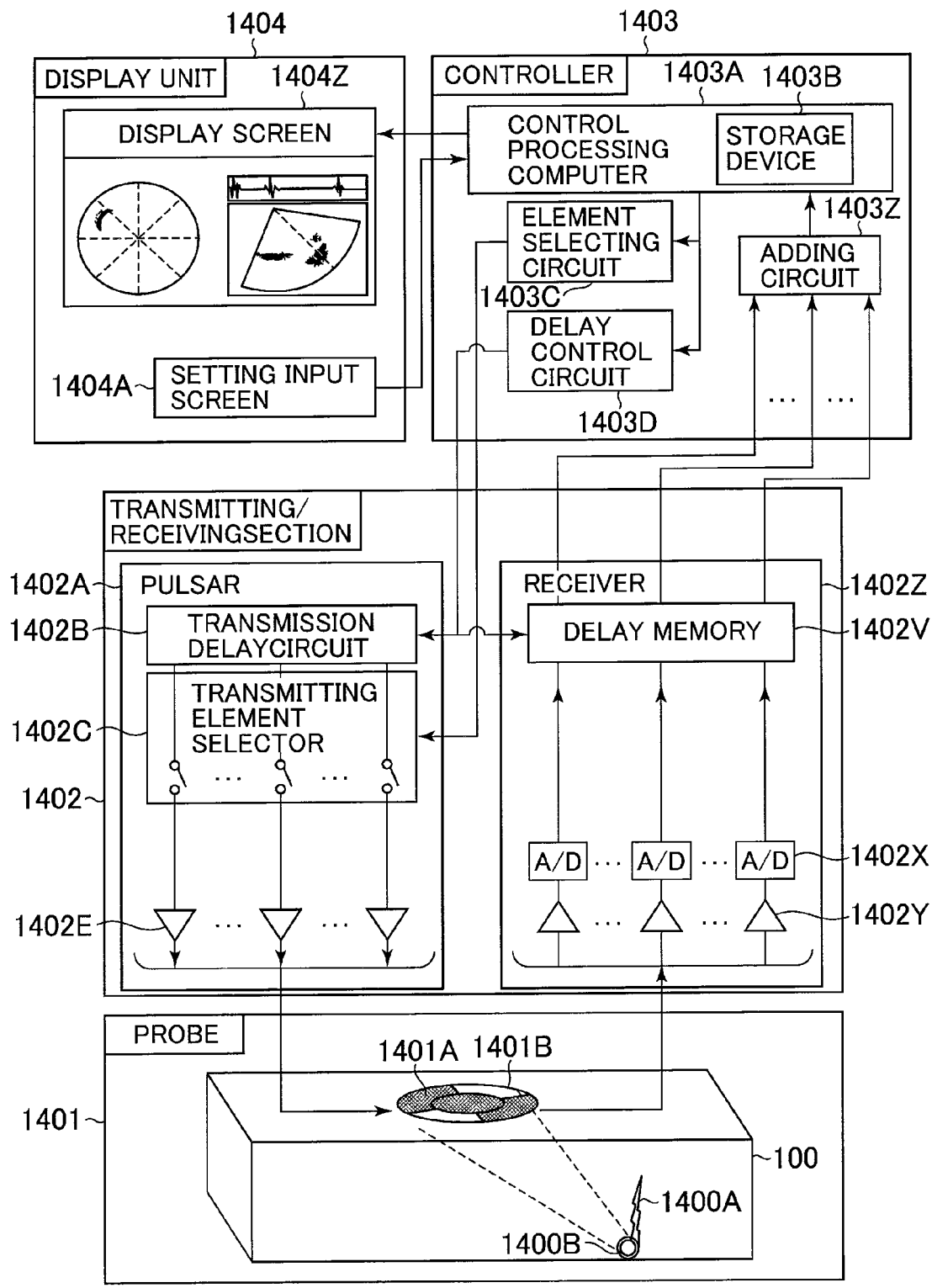
FIG. 24 is a block diagram showing the configuration of an ultrasonic measurement apparatus according to a fifth embodiment of the present invention.

FIG. 24 is a block diagram showing the configuration of the ultrasonic measurement apparatus according to the fifth embodiment of the present invention.

The ultrasonic measurement apparatus according to the present embodiment measures a reflection source 1400A that is located in an inner portion of an object 1400 or on the surface of the object 1400 while obtaining an excellent SN ratio. The object 1400 is a plate material having a thickness of 200 mm to 300 mm, for example.

The ultrasonic measurement apparatus according to the present embodiment includes a probe 1401, a transmitting/receiving section 1402, a controller 1403 and a display unit 1404. The probe 1401 has an array sensor 1401B that transmits and receives an ultrasonic wave to and from the object 1400. The array sensor 1401B has a plurality of ultrasonic transducer elements 1401A.

The transmitting/receiving section 1402 includes a pulsar 1402A and a receiver 1402Z. The pulsar 1402A provides a delay time to each of the ultrasonic transducer elements 1401A. Each ultrasonic transducer element 1401A transmits an ultrasonic wave after a time specified by the delay time. The receiver 1402Z receives the ultrasonic wave and converts the received analog ultrasonic wave into a digital signal as a reception signal.

The controller 1403 has a control processing computer 1403A, an element selecting circuit 1403C, a delay time control circuit 1403D and an adding circuit 1403Z. The control processing computer 1403A has a storage device 1403B.

The element selecting circuit 1403C switches between ultrasonic transducer elements 1401A to select a transmitting element (that transmits an ultrasonic wave) and a receiving element (that receives an ultrasonic wave). The delay time control circuit 1403D controls a delay time for transmission and a delay time for reception. The adding circuit 1403Z adds a plurality of signals received from the receiver 14022. The control processing computer 1403A controls the element selecting circuit 1403C, the delay time control circuit 1403D and the adding circuit 1403Z. The control processing computer 1403A stores the received signals in the storage device 1403B and performs processing on the received signals.

The display unit 1404 has a setting input screen 1404A and a display screen 1404Z. Various settings can be displayed on and input through the setting input screen 1404A. The received signals and an image obtained by a measurement are displayed on the display screen 1404Z.

Next, operations of the sections of the ultrasonic measurement apparatus are described.

The control processing computer 1403A transmits a transmitting/receiving element switching signal that is used to select an ultrasonic transducer element to be used to transmit/receive an ultrasonic wave to the element selecting circuit 1403C, upon storing a reflection signal received from an object to be measured by transmission and reception of an ultrasonic wave. In addition, the control processing computer 1403A provides, through the delay control circuit 1403D, a delay time to each ultrasonic transducer element so that the element transmits an ultrasonic wave that will be focused and receives an ultrasonic wave.

A transmission delay circuit 1402B receives the transmitted signal and the delay time and transmits the signal (transmission signal) to a transmitting element selector 1402C after a time specified by the received delay time. The transmitting element selector 1402C receives the transmission signal having the delay time added thereto from the transmission delay circuit 1402B. Then, the transmitting element selector 1402C selects a transmitting element on the basis of a selection signal that is used to select the transmitting element and is transmitted from the element selecting circuit 1403C, and transmits the transmission signal to a transmission amplifier 1402E.

The adding circuit 1403Z may select a signal that is to be received and corresponds to the transmitted ultrasonic wave, in a similar manner to information that is provided to the element selecting circuit 1403C.

Next, the configuration of the ultrasonic measurement apparatus according to the present embodiment is described with reference to FIGS. 25 and 26.

Figure 25:
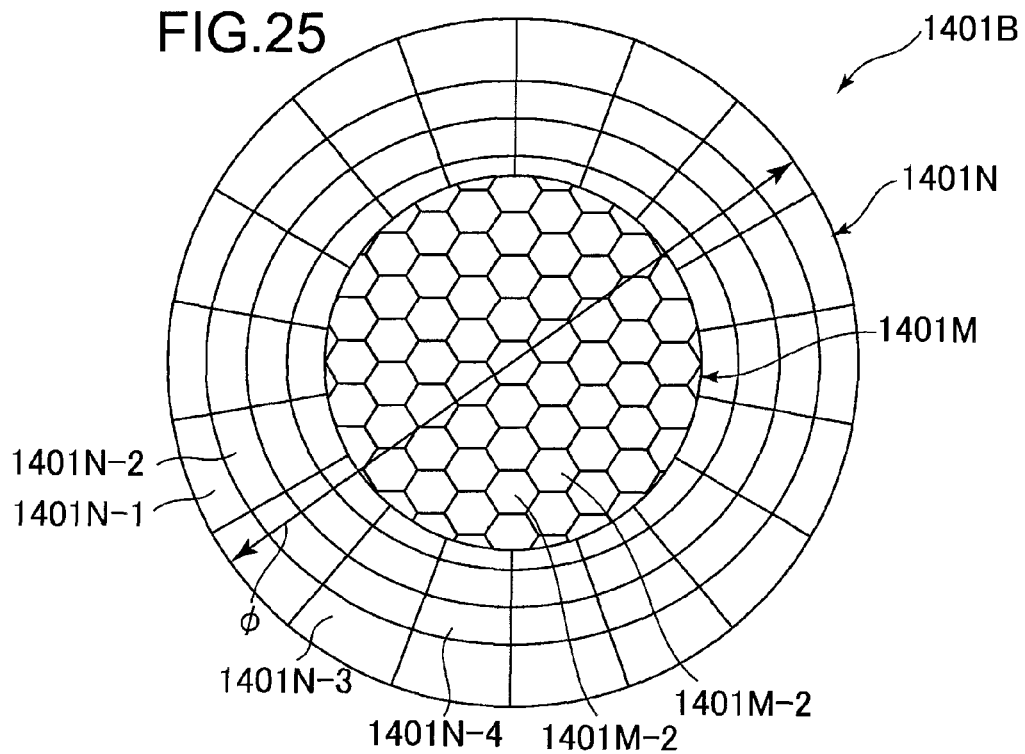
FIG. 25 is a plan view showing the configuration of an array sensor that is used in the ultrasonic measurement apparatus according to the fifth embodiment of the present invention.

FIG. 25 is a plan view of the configuration of the array sensor included in the ultrasonic measurement apparatus according to the fifth embodiment of the present invention. FIG. 26 is a schematic diagram showing the positions of the gravity centers of the elements included in the array sensor that is used in the ultrasonic measurement apparatus according to the fifth embodiment of the present invention.

As shown in FIG. 25, the array sensor 1401B is formed in a circular shape and has a plurality of ultrasonic transducer elements. The array sensor 1401B has an inner circumferential portion 1401M and an outer circumferential portion 1401N. The arrangement of the ultrasonic transducer elements included in the inner circumferential portion 1401M is different from that in the outer circumferential portion 1401N.

The ultrasonic transducer elements included in the inner circumferential portion 1401M are formed in a hexagonal shape and have a flat surface so that the surface of the array sensor can be filled efficiently with the flat surfaces of the elements. The sizes of the ultrasonic transducer elements included in the inner circumferential portion 1401M are the same. In addition, the size of the ultrasonic transducer element included in the inner circumferential portion 1401M is configured so that directivity of ultrasonic waves transmitted from the element included in the inner circumferential portion 1401M is excellent and an image can be obtained with an improved SN ratio by an inspection.

The ultrasonic transducer elements included in the outer circumferential portion 1401N are concentrically arranged around the center of the sensor and are formed in a fan shape. The size of the ultrasonic transducer element included in the outer circumferential portion 1401N is increased toward the outer side of the array sensor.

In the present embodiment, the diameter of a sensor aperture that is considered to be necessary for inspection is $\phi$; a central region having a diameter of $\frac{1}{2}\phi$ is regarded as the inner circumferential portion 1401M; and the other region of the sensor is regarded as the outer circumferential portion 1401N. The diameter of the inner circumferential portion 1401M is preferably in a range of $\frac{1}{4}\phi$ to $\frac{3}{4}\phi$. The reason for the diameter range is described later with reference to FIG. 29.

As described above, the size of the ultrasonic transducer element included in the inner circumferential portion 1401M is configured so that directivity of ultrasonic wave transmitted from the element included in the inner circumferential portion 1401M is excellent and an image can be obtained with an improved SN ratio by an inspection. Each size of the ultrasonic transducer elements included in the outer circumferential portion 1401N is larger than that in the inner circumferential portion 1401M. The size of the ultrasonic transducer element included in the outer circumferential portion 1401N is increased toward the outer side of the array sensor. Therefore, even when the diameter $\phi$ of the sensor aperture is increased, the number of the elements that constitute the array sensor 1401B is not increased.

Next, the gravity centers of the elements that constitute the array sensor 1401A shown in FIG. 25 are described with reference to FIG. 26. Black dots shown in FIG. 26 denote the gravity centers of the elements.

The elements included in the inner circumferential portion 1401M are formed in a hexagonal shape so that sides of adjacent elements are in contact with each other. Distances L1 between adjacent pairs of the ultrasonic transducer elements included in the inner circumferential portion 1401M are the same.

The elements included in the outer circumferential portion 1401N are concentrically arranged around the center of the sensor and are formed in a fan shape. Thus, a distance L3 which is measured in the circumferential direction of the sensor, between the gravity centers of each adjacent pair of the ultrasonic transducer elements, is larger than a distance L2 which is measured in a radial direction of the sensor, between the gravity centers of each adjacent pairs of the ultrasonic transducer elements. In addition, the distance L2 which is measured in the radial direction of the sensor, between the gravity centers of each adjacent pair of the ultrasonic transducer elements, is the same as the distance L1 between each adjacent pair of the ultrasonic transducer elements included in the inner circumferential portion 1401M.

Next, a relationship between distances between adjacent pairs of the elements and occurrence of noise (grating lobe) is described below.

In general, when an array sensor having elements is used, and $L0 \leq (\lambda/(1+|\sin \theta|))$ is established, where L0 is a distance between gravity centers of each adjacent pair of the elements and $\theta$ is an angle at which an ultrasonic wave is transmitted and received, noise (grating lobe) does not occur.

A symbol $\lambda$ indicates the wavelength of the ultrasonic wave transmitted and received. For example, when an ultrasonic wave is transmitted and received to and from a region ranging from −90 degrees to +90 degrees and $L0 \leq \lambda/2$, noise (grating lobe) does not occur. When an ultrasonic wave is transmitted and received to and from a region ranging from −30 degrees to +30 degrees and $L0 \leq \lambda/1.5$, noise (grating lobe) does not occur.

The distance L1 between the gravity centers of each adjacent pair of the ultrasonic transducer elements included in the inner circumferential portion 1401M of the array sensor 1401B is equal to or less than the distance L0 that does not cause noise (grating lobe).

In addition, the distance L2 which are arranged in the radial direction of the array sensor 1401B, between the gravity centers of each adjacent pair of the ultrasonic transducer elements that are included in the outer circumferential portion 1401N of the array sensor 1401B, is equal to or less than the distance L0 that does not cause noise (grating lobe). On the other hand, the distance L3 which is measured in the circumferential direction of the array sensor 1401B, between the gravity centers of each adjacent pair of the ultrasonic transducer elements that are included in the outer circumferential portion 1401N of the array sensor 1401B, is larger than the distance L0 that does not cause noise (grating lobe).

In order to improve an SN ratio, the distances between the gravity centers of adjacent pairs of all the elements need to be equal to or less than the distance L0 that does not cause noise (grating lobe). In order to do so, it is necessary that the lengths of the elements included in the outer circumferential portion 1401N be short in the circumferential direction. In this case, the elements that constitute the array sensor 1401B are made small. Therefore, when the diameter $\phi$ of the aperture is increased, the number of the elements that constitute the array sensor 1401B is increased.

On the other hand, each size of the ultrasonic transducer elements included in the outer circumferential portion 1401N is larger than that in the inner circumferential portion 1401M. In addition, the size of the ultrasonic transducer element included in the outer circumferential portion 1401N is increased toward the outer side of the array sensor 1401B. Thus, even when the diameter $\phi$ of the aperture is increased, the number of the elements that constitute the array sensor 1401B is not increased. However, the distance L3 which is measured in the circumferential direction, between the gravity centers of each adjacent pair of the ultrasonic transducer elements that are included in the outer circumferential portion 1401N, is larger than the distance L0 that does not cause noise (grating lobe). Thus, when the array sensor 1401B is used without a change, noise (grating lobe) may occur.

In the present embodiment, the array sensor 1401B shown in FIG. 25 is used. In order to prevent noise (grating lobe), an element that is to be used to transmit and receive an ultrasonic wave is selected from among the elements that are included in the outer circumferential portion 1401N of the array sensor 1401B on the basis of a transmitting and receiving direction. The distance L1 between the gravity centers of each adjacent pair of the ultrasonic transducer elements included in the inner circumferential portion 1401B is equal to or less than the distance L0 that does not cause noise (grating lobe). Thus, all the elements included in the inner circumferential portion 1401M are used to transmit and receive an ultrasonic wave in all directions. In this case, the transmitting and receiving direction does no indicate an actual direction in which an ultrasonic wave is transmitted and received. The transmitting and receiving direction indicates a direction obtained by projecting the actual transmitting and receiving direction onto the flat surface of the array sensor 1401B.

Figure 26:
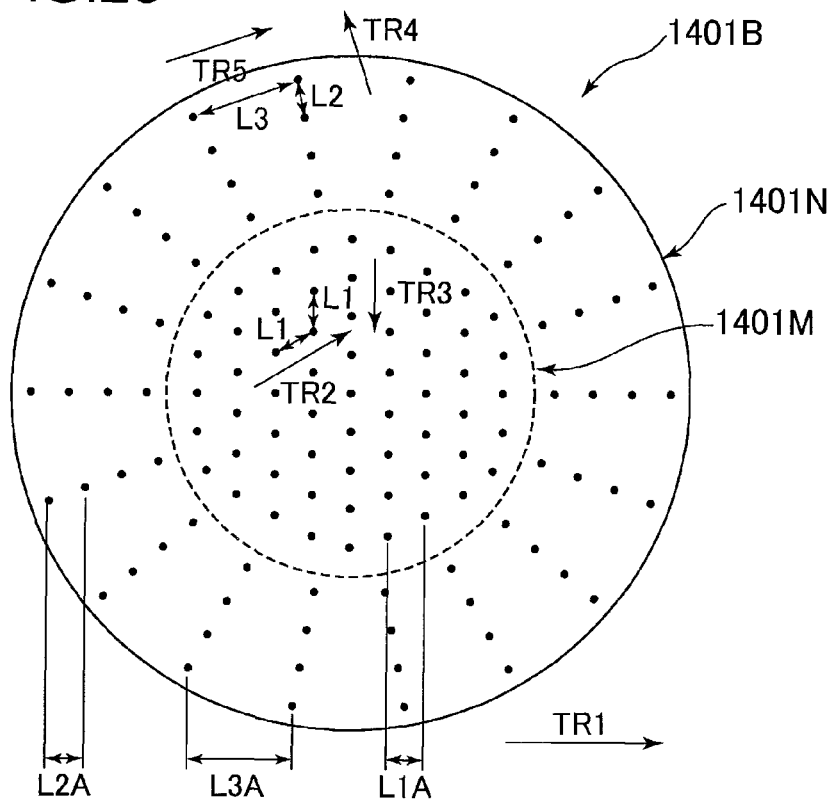
FIG. 26 is a schematic diagram showing the positions of the gravity centers of elements included in the array sensor that is used in the ultrasonic measurement apparatus according to the fifth embodiment of the present invention.

The following describes the case in which an ultrasonic wave is transmitted and received in a direction along an arrow TR1 of FIG. 26. In this case, a distance L1A between the gravity centers of each adjacent pair 1401M-1 and 1401M-2 of the elements included in the inner circumferential portion 1401M, which is measured in the direction shown by the arrow TR1, is equal to or less than the distance L0 (=L1) that does not cause noise (grating lobe). Thus, when the adjacent elements 1401M-1 and 1401M-2 are used for transmission and reception, noise (grating lobe) does not occur.

In addition, a distance L2A which is measured in the direction shown by the arrow TR1, between the gravity centers of each adjacent pair 1401N-1 and 1401N-2 of the elements that are included in the outer circumferential portion 1401N, is equal to or less than the distance L0 (=L2) that does not cause noise (grating lobe). Thus, when the adjacent elements 1401N-1 and 1401N-2 are used for transmission and reception, noise (grating lobe) does not occur.

However, a distance L3A which is measured in the direction shown by the arrow TR1, between the gravity centers of each adjacent pair 1401N-3 and 1401N-4 of the elements that are included in the outer circumferential portion 1401N and are arranged in the circumferential direction, is larger than the distance L0 (=L2) that does not cause noise (grating lobe). Thus, when the adjacent elements 1401N-3 and 1401N-4 are used for transmission and reception, noise (grating lobe) may occur.

When ultrasonic waves are to be transmitted and received in the direction shown by the arrow TR1, the pair of elements 1401M-1 and 1401M2 and the pair of elements 1401N-1 and 1401N-2 are used and the pair of elements 1401N-3 and 1401N-4 is not used to prevent noise (grating lobe).

It is assumed that elements that are adjacent to each other with the distance L1 and are included in the inner circumferential portion 1401M transmit and receive an ultrasonic wave in directions along arrows TR2 and TR3 of FIG. 26. In this assumption, distances between the gravity centers of the adjacent elements, which are measured in the direction shown by any of the arrows TR2 and TR3, are equal to or less than the distance L0 (=L1) that does not cause noise (grating lobe). Thus, even when the adjacent elements are used for transmission and reception, noise (grating lobe) does not occur.

The distance L1 between the gravity centers of each adjacent pair of the ultrasonic transducer elements included in the inner circumferential portion 1401M is equal to or less than the distance L0 that does not cause noise (grating lobe). Thus, even when all the elements included in the inner circumferential portion 1401M are used for transmission and reception, noise (grating lobe) does not occur.

It is assumed that elements that are adjacent to each other with the distance L2 and are included in the outer circumferential portion 1401N transmit or receive an ultrasonic wave in a direction along an arrow TR4 of FIG. 26. In this assumption, a distance which is measured in the direction shown by the arrow TR4, between the gravity centers of the adjacent elements, is equal to or less than the distance L0 (=L2) that does not cause noise (grating lobe). Thus, even when the adjacent elements are used for transmission and reception, noise (grating lobe) does not occur.

It is assumed that elements that are adjacent to each other with the distance L3 and are included in the outer circumferential portion 1401N transmit or receive an ultrasonic wave in a direction along an arrow TR5 of FIG. 26. In this assumption, a distance which is measured in the direction shown by the arrow TR5, between the gravity centers of the adjacent elements, is larger than the distance L0 (=L2) that does not cause noise (grating lobe). Thus, when the adjacent elements are used for transmission and reception, noise (grating lobe) may occur. Therefore, when ultrasonic waves are to be transmitted and received in the direction shown by the arrow TR5, the elements that are adjacent to each other with the distance L3 are not used.

The array sensor 1401B (shown in FIG. 25) according to the present embodiment is characterized in that the distance between the gravity centers of each adjacent pair of the elements that are included in the inner circumferential portion 1401M is equal to or less than a specified distance that is the distance L0 (that does not cause noise (grating lobe)). On the other hand, in the outer circumferential portion 1401N, some of the distances between the gravity centers of adjacent pairs of the elements are equal to or less than the specified distance, while the others of the distances between the gravity centers of the adjacent pairs of the elements are separated with each other with the distance larger than the specified distance.

The elements included in the inner circumferential portion 1401M may be formed in a triangular, quadrangular, or trapezoidal shape, in addition to the hexagonal shape. The trapezoidal shape is formed by dividing the hexagonal shape shown in FIG. 25 into two along the diagonal of the hexagon shown in FIG. 25.

The elements included in the outer circumferential portion 1401N may be formed in a polygonal shape that is formed by radially dividing the sensor into pieces along a line that passes through the center of the sensor, in addition to the shape of the elements that are concentrically arranged.

Since the array sensor includes the inner and outer circumferential portions, the sensor aperture is large. Thus, the array sensor is capable of inspecting a deep portion. In addition, elements that are to be used for transmission and reception are selected from the elements included in the outer circumferential portion of the array sensor on the basis of the transmitting and receiving direction. Thus, an SN ratio can be improved while noise (grating lobe) does not occur.

Next, an inspection method that is performed by the ultrasonic measurement apparatus according to the present embodiment is described with reference to FIGS. 27 and 28.

Figure 27:
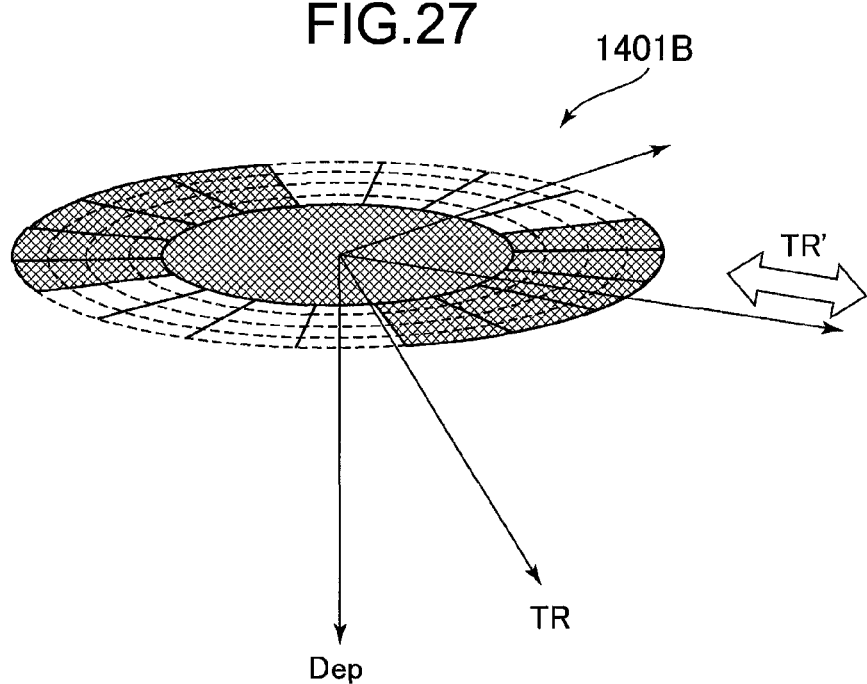
FIG. 27 is a diagram showing an inspection method that is performed by the ultrasonic measurement apparatus according to the fifth embodiment of the present invention.

FIG. 27 is a diagram showing the inspection method that is performed by the ultrasonic measurement apparatus according to the present embodiment. FIG. 28 is a diagram showing the array sensor that is used in the ultrasonic measurement apparatus according to the present embodiment.

When an ultrasonic wave is to be transmitted and received by the 2D array sensor having the structure shown in FIGS. 25 and 26, the ultrasonic transducer elements included in the inner circumferential portion 1401M are arranged so that the distance L1 between the gravity centers of each adjacent pair of the elements is equal to or less than the specified distance. Thus, the inner circumferential portion 1401M can be designed so that a noise source is not present. Therefore, all the elements included in the inner circumferential portion 1401M can be used to transmit and receive an ultrasonic wave.

The gravity centers of each adjacent pair of the ultrasonic transducer elements included in the outer circumferential portion 1401N and arranged in the circumferential direction are separated with each other with the distance L3 that is larger than the specified distance. Thus, these ultrasonic transducer elements may become sources of extremely high frequency noise depending on the transmitting and receiving direction.

In FIG. 27, the ultrasonic array sensor 1401B is placed on a flat surface that is perpendicular to a depth direction Dep. The ultrasonic array sensor 1401B transmits an ultrasonic wave and receives a reflected wave in and from an ultrasonic transmitting and receiving direction TR. A transmitting and receiving direction TR' is obtained by projecting the ultrasonic transmitting and receiving direction TR onto a flat surface of the ultrasonic array sensor 1401B.

Figure 28:
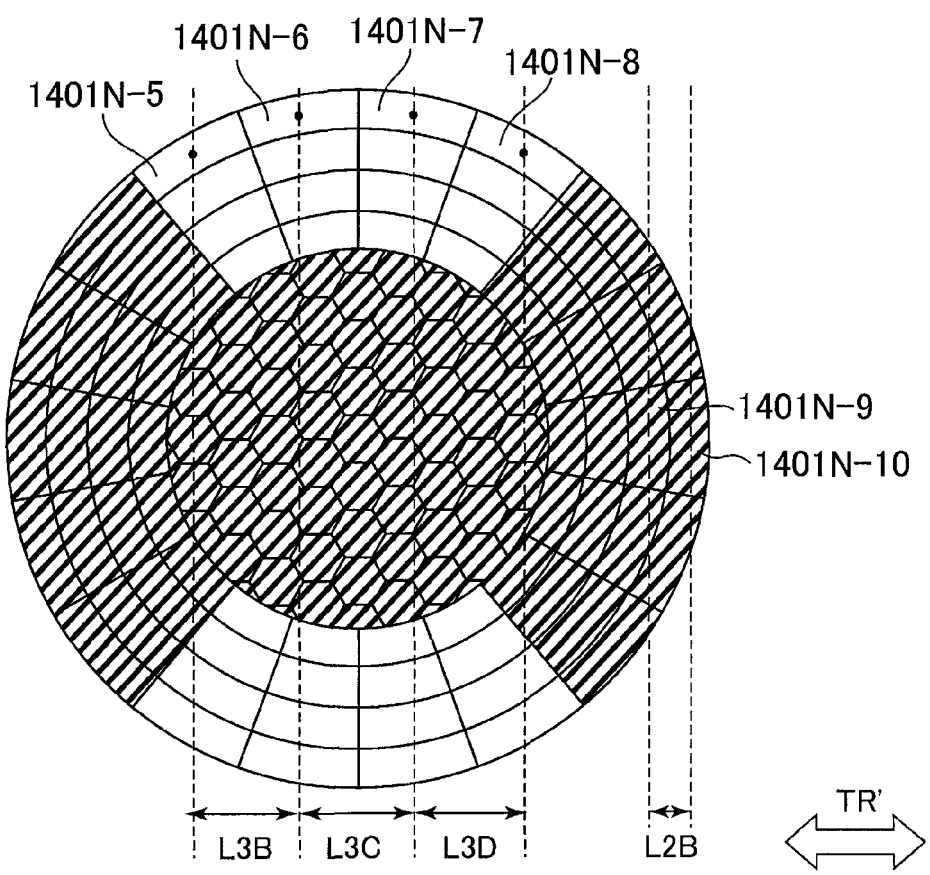
FIG. 28 is a diagram showing the array sensor that is used in the ultrasonic measurement apparatus according to the fifth embodiment of the present invention.

FIG. 28 shows the flat surface of the ultrasonic array sensor 1401B. It is assumed that the gravity centers are projected on axes extending in a direction in which an ultrasonic wave is transmitted and received, and the direction is projected onto the flat surface of the array sensor 1401B to form an ultrasonic transmitting and receiving direction TR'. In this assumption, elements that are arranged on axes perpendicular to the ultrasonic transmitting and receiving direction TR' and are included in the outer circumferential portion 1401N are denoted by 1401N-5, 1401N-6, 1401N-7 and 1401N-8. A distance which is measured in the ultrasonic transmitting and receiving direction TR', between the gravity centers of the elements 1401N-5 and 1401N-6, is denoted by L3B. A distance which is measured in the ultrasonic transmitting and receiving direction TR', between the gravity centers of the elements 1401N-6 and 1401N-7, is denoted by L3C. A distance which is measured in the ultrasonic transmitting and receiving direction TR', between the gravity centers of the elements 1401N-7 and 1401N-8, is denoted by L3D. The distances L3B, L3C and L3D are larger than the distance L0 that does not cause noise (grating lobe). When the elements that are adjacent to each other with the distance L3B, L3C and L3D transmit ultrasonic waves, a high-frequency ultrasonic wave that is called a grating lobe may occur and propagate in an unwanted direction.

Elements arranged in the ultrasonic transmitting and receiving direction TR' are denoted by 1401N-9 and 1401N-10. A distance L2B which is measured in the ultrasonic transmitting and receiving direction TR', between the gravity centers of the elements 1401N-9 and 1401N-10, is smaller than the distance L0 that does not cause noise (grating lobe). Thus, a grating lobe does not occur.

When elements (shown by hatching lines in FIG. 28) whose projected gravity centers are separated with each other with a distance that is equal to or less than the specified distance are selected, an inspection can be performed while an excellent SN ratio is obtained. In other words, when all the elements included in the inner circumferential portion and some of the elements included in the outer circumferential portion are selected, an inspection can be performed while an excellent SN ratio is obtained.

Next, a method for selecting an element to be used in the ultrasonic measurement apparatus according to the present embodiment, from among the elements of the sensor is described with reference to FIG. 29.

Figure 29:
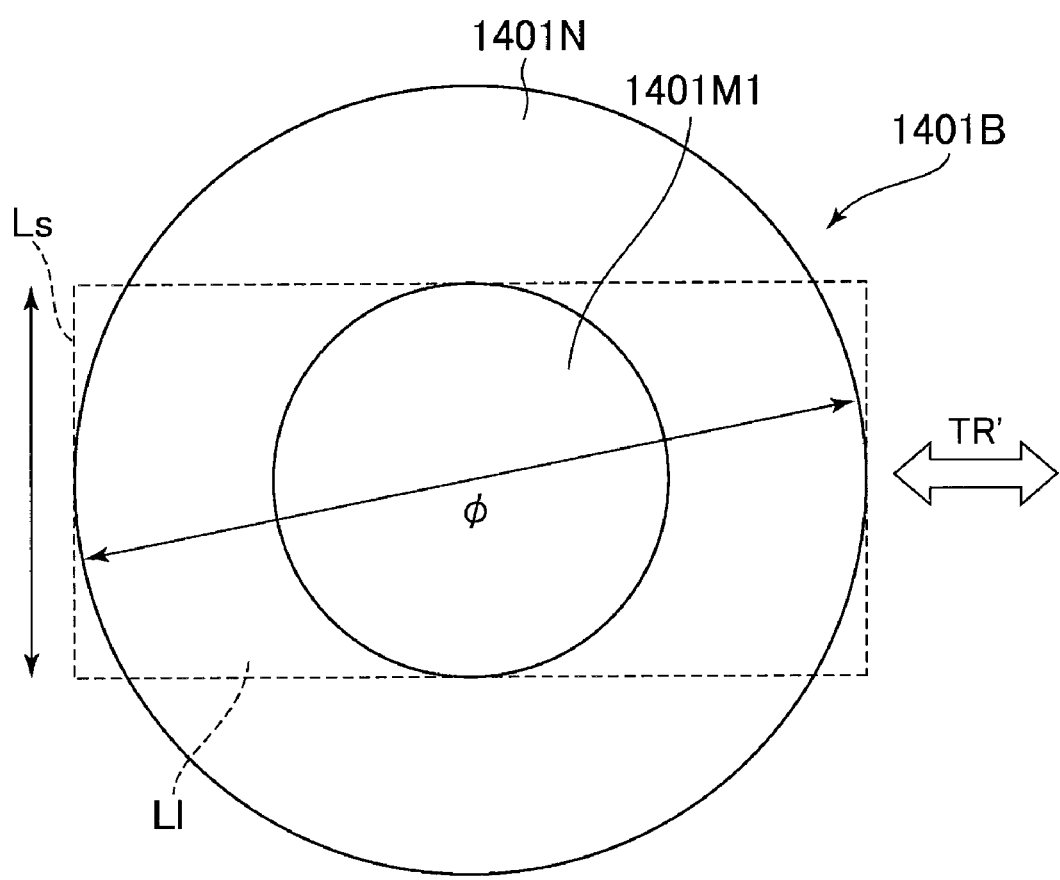
FIG. 29 is a diagram showing a method for selecting an element that is included in the sensor that is used in the ultrasonic measurement apparatus according to the fifth embodiment of the present invention.

FIG. 29 is a diagram showing the method for selecting an element to be used in the ultrasonic measurement apparatus according to the present embodiment, from among the elements of the sensor.

In order to use all the ultrasonic transducer elements included in the inner circumferential portion 1401N and some of the ultrasonic transducer elements included in the outer circumferential portion 1401M as described with reference to FIG. 28, ultrasonic transducer elements are selected as shown in FIG. 29.

Specifically, the following elements are used to perform an inspection: elements whose gravity centers are located in a region surrounded by a dashed line shown in FIG. 29 and which are arranged in the projected ultrasonic transmitting and receiving direction TR'. In this case, the rectangular region surrounded by the dashed line includes the inner circumferential portion of the sensor in general. In other words, the length of a short side Ls of the rectangular region is equal to the diameter of the inner circumferential portion 1401M of the array sensor 1401B. The length of a long side Ll of the rectangular region is equal to or larger than the diameter (measured in the projected transmitting and receiving direction TR') of the outer circumferential portion 1401N of the array sensor 1401B.

When the diameter of the inner circumferential portion 1401M is ½φ (φ is the diameter of the sensor aperture) as described with reference to FIG. 25, the ratio of the short side Ls to the long side Ll is ½. When the diameter of the inner circumferential portion 1401M is in a range of ¼φ to ¾φ, the ratio of the short side Ls to the long side Ll is in a range of ¼ to ¾.

Next, the inspection method that is performed by the ultrasonic measurement apparatus according to the present embodiment is described with reference to FIG. 30.

Figure 30:
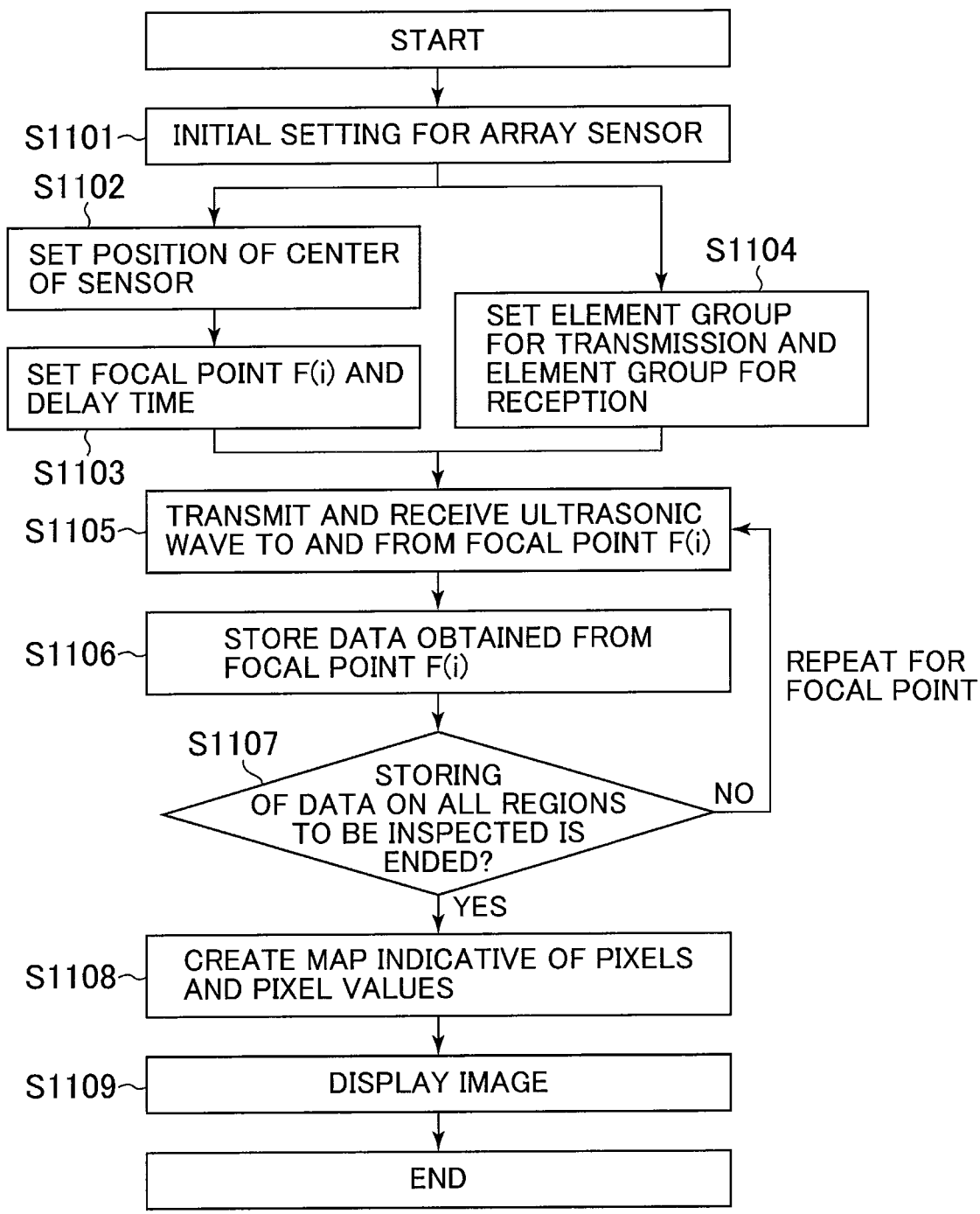
FIG. 30 is a flowchart showing content of the inspection method that is performed by the ultrasonic measurement apparatus according to the fifth embodiment of the present invention.

FIG. 30 is a flowchart showing the content of the inspection method that is performed by the ultrasonic measurement apparatus according to the present embodiment.

When the setting is started, the inspector uses the setting input screen 1404A (shown in FIG. 24) to enter, as initial settings for the array sensor, necessary information such as information on the ultrasonic transducer elements that constitute the array sensor 1401B shown in FIG. 25 (sizes, arrangements and positions of the elements) and the velocity of an ultrasonic wave in step S1101.

Next, the position of the center of the sensor having the N number of ultrasonic transducer elements, which is a reference of the delay time and image display, is set on the setting input screen 1404A in step S1102. In general, the center (intersection of a central line Cy and a central line Cx) of the ultrasonic transducer elements is set as the center C of the sensor.

Next, the control processing computer 1403A calculates a focal point F on which an ultrasonic wave transmitted by each ultrasonic transducer element included in the array sensor is focused, and a delay time for transmission by each ultrasonic transducer element included in the array sensor, and sets the focal point F and the delay time in step S1103.

Meanwhile, the element selecting circuit 1103C uses the information provided in the initial setting of step S1101 to set an ultrasonic transducer element group that is to be used for transmission and reception while the ultrasonic transducer element group does not include elements that causes noise in step S1104.

Then, in order to transmit and receive an ultrasonic wave to and from the focal point F (i) specified in step S1103, the element selecting circuit 1103C selects an element group (element pattern) that is suitable for the transmitting/receiving direction.

The element group (element pattern) that is to be used and is included in the ultrasonic measurement apparatus according to the present embodiment is described with reference to FIGS. 31 and 32.

Figure 32:
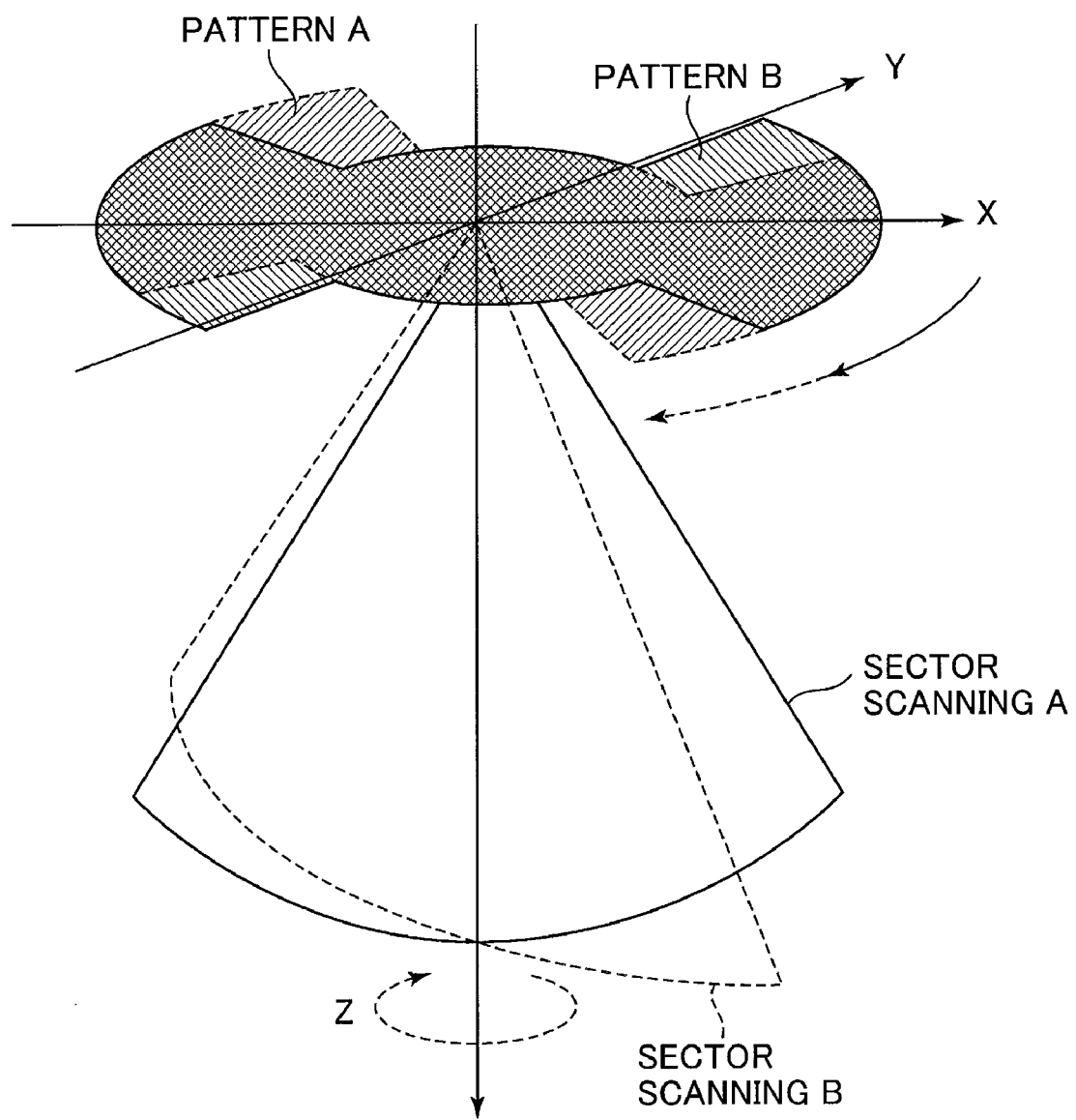
FIG. 32 is a diagram showing a pattern of elements that are to be used and are included in the ultrasonic measurement apparatus according to the fifth embodiment of the present invention.

FIGS. 31 and 32 are diagrams each showing an element pattern that is to be used and is included in the ultrasonic measurement apparatus according to the present embodiment.

FIG. 31 shows a table of an element pattern that is to be used. The table shown in FIG. 31 is pre-stored in the storage device 1403B (shown in FIG. 24). The table includes patterns A, B and C. An element that is to be used is indicated by "1", while an element that is not to be used is indicated by "0".

In the pattern A, elements that are to be used as shown in FIG. 32 are selected. In the pattern B, elements that are to be used as shown in FIG. 32 are selected. When the pattern A is used, sector scanning A is performed as shown in FIG. 32. When the pattern B is used, sector scanning B is performed as shown in FIG. 32.

Each of the patterns A, B and C is associated with an ultrasonic transmitting and receiving direction. Thus, when the ultrasonic transmitting and receiving direction is determined, a pattern necessary for transmission and reception can be selected.

In order to transmit and receive an ultrasonic wave to and from the focal point F (i) specified in step S1103, the element selecting circuit 1103C selects the element pattern described with reference to FIGS. 31 and 32 in step S1105 shown in FIG. 30, and the pulsar 1402A transmits an ultrasonic wave in step S1105.

Then, the receiver 1402Z stores data (reflection data) on the focal point F (i) in step S1106.

Next, the control processing computer 1403A determines whether or not storing of data on all regions is ended, in step S1107. When the storing is not ended (or when the answer in step S1107 is NO), the process returns to S1105 and is performed on the next focal point F (i+1). Then, an ultrasonic wave is transmitted and received again and reflection data is stored. Steps S1105 and S1106 are repeated until reflection data on all the regions to be measured is stored.

When it is determined that the storing of data on all the regions is ended (or when the answer in step S1107 is YES), the control processing computer 1403A creates a map indicative of pixels and pixel values in step S1108 and causes an image to be displayed, in step S1109. Then, the process is ended.

A necessary sector-scanned image can be obtained by selecting one of the patterns shown in FIG. 31. Thus, many sector-scanned images can be stored by electronically switching between the patterns A and B shown in FIG. 32. In addition, a 3D image can be obtained with a high SN ratio even from a deep portion.

Next, another configuration of the array sensor that is used in the ultrasonic measurement apparatus according to the present embodiment is described with reference to FIG. 33.

Figure 33:
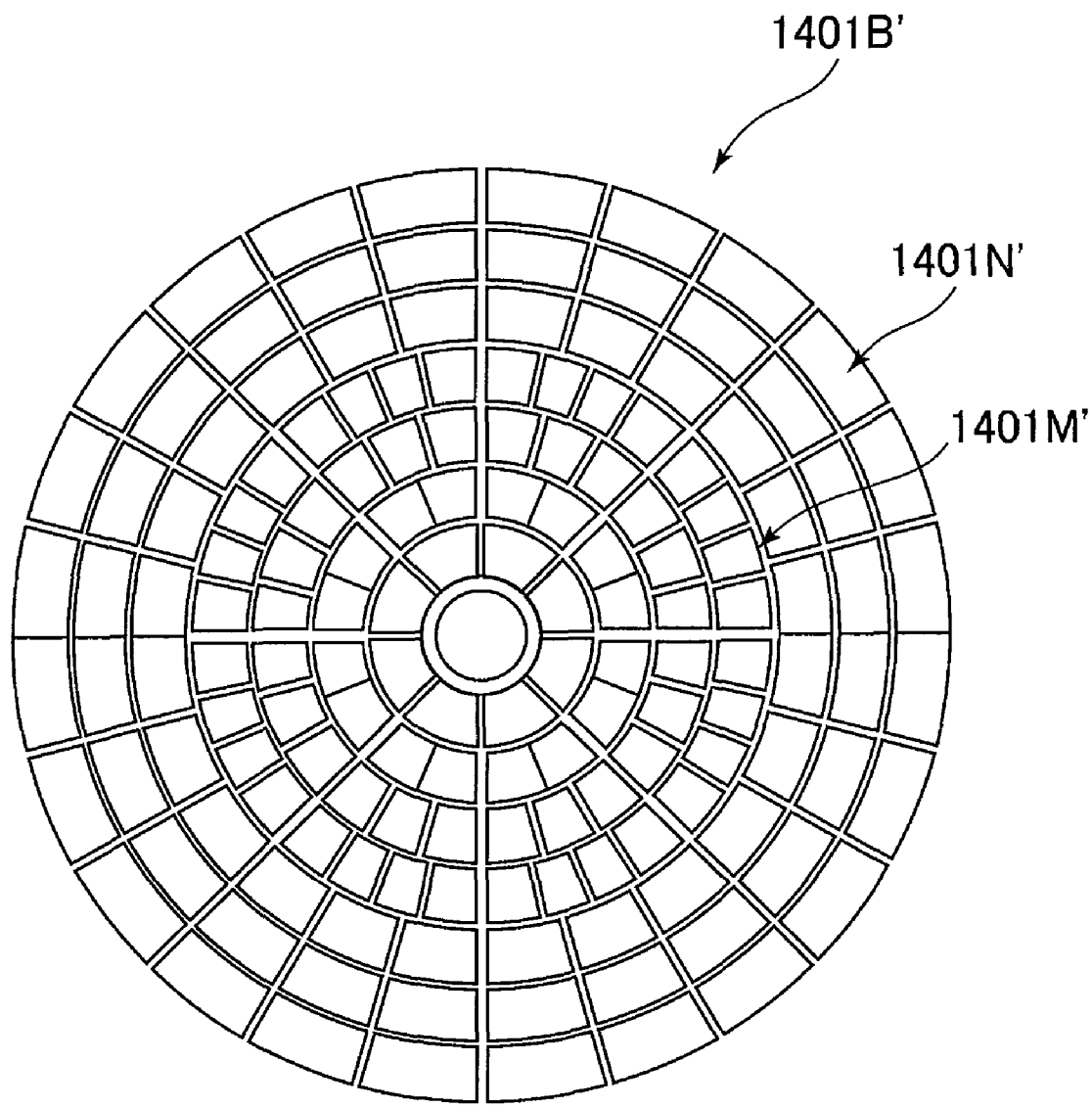
FIG. 33 is a plan view of another configuration of the array sensor that is used in the ultrasonic measurement apparatus according to the fifth embodiment of the present invention.

FIG. 33 is a plan view of the configuration of the array sensor that is used in the ultrasonic measurement apparatus according to the present embodiment.

As shown in FIG. 33, the array sensor 1401B' is formed in a circular shape and has a plurality of ultrasonic transducer elements. The array sensor 1401B' has an inner circumferential portion 1401M' and an outer circumferential portion 1401N'. The arrangement of ultrasonic transducer elements included in the inner circumferential portion 1401M' is different from the arrangement of ultrasonic transducer elements included in the outer circumferential portion 1401N'.

The ultrasonic transducer elements included in the inner circumferential portion 1401M' are arranged as follows. The ultrasonic transducer element located in the innermost circumference of the portion 1401M' is not segmented, the element located in the second circumference (that is adjacent to and located on the outer side of the innermost circumference) of the portion 1401M' is segmented into 8 elements, the element located in the third circumference (that is adjacent to and located on the outer side of the second circumference) of the portion 1401M' is segmented into 16 elements, the element located in the fourth circumference (that is adjacent to and located on the outer side of the third circumference) of the portion 1401M' is segmented into 24 elements, and the element located in the fifth circumference (that is adjacent to and located on the outer side of the fourth circumference) of the portion 1401M' is segmented into 32 elements. As described above, the number of the segmented elements is increased toward the outer circumferential side. The sizes of the segmented ultrasonic transducer elements included in the inner circumferential portion 1401M' are not exactly the same but almost the same. In addition, the ultrasonic transducer elements included in the inner circumferential portion 1401M' are configured so that directivity of ultrasonic waves transmitted from the elements included in the inner circumferential portion 1401M' is excellent and an image can be obtained with an improved SN ratio by an inspection.

The ultrasonic transducer elements included in the outer circumferential portion 1401N' are concentrically arranged around the center of the array sensor and are formed in a fan shape. The size of the ultrasonic transducer element located in the outer circumferential portion 1401N' is increased toward the outer side of the outer circumferential portion 1401N'.

The ultrasonic transducer elements included in the inner circumferential portion 1401M' are configured so that directivity of ultrasonic waves is excellent and an image can be obtained with an improved SN ratio by an inspection. Each size of the ultrasonic transducer elements included in the outer circumferential portion 1401N' is larger than that in the inner circumferential portion 1401M'. The size of the ultrasonic transducer element included in the outer circumferential portion 1401N' is increased toward the outer circumferential side. Thus, even when the diameter $\phi$ of the sensor aperture is increased, the number of the elements that constitute the array sensor 1401B' is not increased.

As described above, in order to perform an ultrasonic inspection on a deep portion of a plate material having a large thickness, it is necessary that a sensor has a large aperture. However, since the number of elements is restricted, it is difficult that a conventional existing 2D array sensor has a large aperture. According to the present invention, the ultrasonic array sensor has the inner and outer circumferential portions while the arrangement of the elements included in the inner circumferential portion is different from that in the outer circumferential portion. Thus, the array sensor is capable of having a large aperture. In addition, since some of the elements included in the outer circumferential portion are used to transmit and receive an ultrasonic wave, the array sensor can suppress occurrence of noise. Furthermore, it is possible to inspect a deep portion of a plate material having a large thickness by using the sensor having the large aperture while obtaining a high SN ratio and maintaining the point focusing effect.

It is, therefore, possible to inspect a deep portion of a plate material having a large thickness by using a small number of ultrasonic transducer elements while obtaining a high SN ratio and maintaining the point focusing effect.

What is claimed is:

1. An ultrasonic measurement method using a two-dimensional array sensor that has a plurality of ultrasonic transducer elements two-dimensionally arranged and using a wave reflected from an inner portion of an object that is to be measured, comprising the steps of:

selecting a group of a plurality of ultrasonic transducer elements for transmission from among the ultrasonic transducer elements that constitute the two-dimensional array sensor so that the ultrasonic transducer elements selected for transmission are arranged in line symmetry with respect to a first line symmetric axis and setting the group selected for transmission, and selecting a group of a plurality of ultrasonic transducer elements for reception from among the ultrasonic transducer elements that constitute the two-dimensional array sensor so that the ultrasonic transducer elements selected for reception are arranged in line symmetry with respect to a second line symmetric axis that is perpendicular to the first line symmetric axis and passes through a rotationally symmetric axis and setting the group selected for reception;

transmitting an ultrasonic wave in the direction of the first line symmetric axis;

receiving an ultrasonic wave from the direction of the second line symmetric axis to store a signal reflected from the inner portion of the object; and processing the reflected signal to inspect the object.

2. The ultrasonic measurement method according to claim 1, further comprising the steps of:

selecting a group of a plurality of ultrasonic transducer elements for transmission from among the ultrasonic transducer elements that constitute the two-dimensional array sensor so that the ultrasonic transducer elements selected for: transmission are arranged in line symmetry with respect to a third line symmetric axis that is set by rotating the first line symmetric axis by a predetermined angle with respect to the rotationally symmetric axis, and selecting a group of a plurality of ultrasonic transducer elements for reception from among the ultrasonic transducer elements that constitute the two-dimensional array sensor so that the ultrasonic transducer elements selected for reception are arranged in line symmetry with respect to a fourth line symmetric axis that is perpendicular to the third line symmetric axis and passes through the rotationally symmetric axis;

transmitting an ultrasonic wave in the direction of the third line symmetric axis;

receiving an ultrasonic wave from the direction of the fourth line symmetric axis to store a signal reflected from the inner portion of the object; and processing the reflected signal to inspect the object.

3. The ultrasonic measurement method according to claim 1, wherein, the group of the ultrasonic transducer elements selected for transmission and the group of the ultrasonic transducer elements selected for reception are arranged so that when the groups are rotated about the rotationally symmetric axis by 90 degrees, the groups overlap each other.

4. The ultrasonic measurement method according to claim 1, further comprising the steps of:

setting a plurality of focal points to which ultrasonic waves are to be transmitted by the two-dimensional array sensor;

storing signals reflected from the focal points that are located in the inner portion of the object; and processing the stored reflected signals to two-dimensionally or three-dimensionally image the inner portion of the object and display an image of the inner portion of the object.

5. The ultrasonic measurement method according to claim 4, further comprising the step of:

projecting three-dimensionally stored measurement data onto a flat plane and two-dimensionally displaying the data on an inspection result display screen.

6. The ultrasonic measurement method according to claim 5, further comprising the step of displaying information on a refraction angle $\phi$, an azimuth angle $\theta$ and a reflected intensity I.

7. The ultrasonic measurement method according to claim 6, further comprising the step of specifying a range of the refraction angle $\phi$ to be displayed.

8. The ultrasonic measurement method according to claim 1, further comprising the stops of:

performing either an operation for weighting a pulse voltage that is to be applied to each ultrasonic transducer element selected for transmission before the transmission of the ultrasonic wave or an operation for weighting a signal received when the ultrasonic wave is received; and calibrating reflection data and a reflected intensity.

9. An ultrasonic measurement apparatus comprising:

a two-dimensional array sensor having a plurality of ultrasonic transducer elements two-dimensionally arranged;

a transmitting/receiving section that transmits an ultrasonic wave from each ultrasonic transducer element included in the two-dimensional array sensor to an object to be measured and receives a wave reflected from the object;

a controller that controls the transmitting/receiving section to generate three-dimensional or two-dimensional image data; and a display unit that displays the three-dimensional or two-dimensional image data generated by the controller, wherein the controller includes an element selecting section that selects a group of a plurality of ultrasonic transducer elements for transmission from among the ultrasonic transducer elements that constitute the two-dimensional array sensor so that the ultrasonic transducer elements selected for transmission are arranged in line symmetry with respect to a first line symmetric axis to set the group selected for transmission, and selects a group of a plurality of ultrasonic transducer elements for reception from among the ultrasonic transducer elements that constitute the two-dimensional array sensor so that the ultrasonic transducer elements selected for reception are arranged in line symmetry with respect to a second line symmetric axis that is perpendicular to the first line symmetric axis and passes through a rotationally symmetric axis to set the group selected for reception, and the transmitting/receiving section includes a transmitting element selector and a receiving clement selector, the transmitting element selector being adapted to select, as transmitting elements, the ultrasonic transducer elements set by the clement selecting section, the receiving element selector being adapted to select, as receiving elements, the ultrasonic transducer elements set by the element selecting section.

10. The ultrasonic measurement apparatus according to claim 9, wherein the controller includes either an amplitude adjusting section or a weighting section, the amplitude adjusting section being adapted to weight a pulse voltage that is to be applied to each ultrasonic transducer element selected for transmission before the transmission of the ultrasonic wave, the weighting section being adopted to weight a signal received when the ultrasonic wave is received.

* * * * *